US008417462B2

(12) United States Patent
Bogoch et al.

(10) Patent No.: US 8,417,462 B2
(45) Date of Patent: *Apr. 9, 2013

(54) SYSTEM AND METHOD FOR IDENTIFYING COMPLEX PATTERNS OF AMINO ACIDS

(76) Inventors: Samuel Bogoch, New York, NY (US); Elenore S. Bogoch, New York, NY (US); Samuel Winston Bogoch, Oakland, CA (US); Anne Elenore Borsanyi, Brookline, MA (US)

(*) Notice: Subject to any disclaimer, the term of this patent is extended or adjusted under 35 U.S.C. 154(b) by 398 days.

This patent is subject to a terminal disclaimer.

(21) Appl. No.: 12/349,955

(22) Filed: Jan. 7, 2009

(65) Prior Publication Data

US 2010/0278860 A1 Nov. 4, 2010

Related U.S. Application Data

(63) Continuation of application No. 11/116,203, filed on Apr. 28, 2005, now Pat. No. 7,774,144, and a continuation-in-part of application No. 10/189,437, filed on Jul. 8, 2002, now Pat. No. 7,452,963, which is a continuation-in-part of application No. 10/105,232, filed on Mar. 26, 2002, now Pat. No. 7,189,800, which is a continuation-in-part of application No. 09/984,057, filed on Oct. 26, 2001, now Pat. No. 7,420,028, said application No. 11/116,203 is a continuation-in-part of application No. 10/860,050, filed on Jun. 4, 2004, now Pat. No. 7,442,761.

(60) Provisional application No. 60/565,847, filed on Apr. 28, 2004, provisional application No. 60/653,083, filed on Feb. 16, 2005.

(51) Int. Cl.
*G01N 33/50* (2006.01)

(52) U.S. Cl. ......................................................... 702/19

(58) Field of Classification Search ........................ None
See application file for complete search history.

(56) References Cited

U.S. PATENT DOCUMENTS

| | | | |
|---|---|---|---|
| 4,132,769 A | 1/1979 | Osther |
| 5,104,854 A | 4/1992 | Schlesinger et al. |
| 5,231,167 A | 7/1993 | Zanetti |
| 5,280,113 A | 1/1994 | Rademacher |
| 5,679,352 A | 10/1997 | Chong |
| 5,866,690 A | 2/1999 | Bogoch |
| 6,023,659 A | 2/2000 | Seilhamer et al. |
| 6,070,126 A | 5/2000 | Kokolus et al. |
| 6,090,406 A | 7/2000 | Popescu et al. |
| 6,242,578 B1 | 6/2001 | Bogoch |
| 6,256,647 B1 | 7/2001 | Toh |
| 6,470,277 B1 | 10/2002 | Chin et al. |
| 6,484,166 B1 | 11/2002 | Maynard |
| 6,638,505 B2 | 10/2003 | Bogoch et al. |
| 7,176,275 B2 | 2/2007 | Bogoch et al. |
| 7,189,800 B2 | 3/2007 | Bogoch et al. |
| 7,267,942 B2 | 9/2007 | Peiris |
| 7,420,028 B2 | 9/2008 | Bogoch et al. |
| 7,442,761 B2 | 10/2008 | Bogoch et al. |
| 7,452,963 B2 | 11/2008 | Bogoch et al. |
| 7,674,880 B2 | 3/2010 | Bogoch |
| 7,674,888 B2 | 3/2010 | Perron et al. |
| 7,705,129 B2 | 4/2010 | Bogoch et al. |
| 7,758,863 B2 | 7/2010 | Bogoch et al. |
| 7,763,705 B2 | 7/2010 | Bogoch et al. |
| 7,774,144 B2 | 8/2010 | Bogoch et al. |
| 7,894,999 B2 | 2/2011 | Bogoch et al. |
| 8,050,871 B2 | 11/2011 | Bogoch et al. |
| 2002/0120106 A1 | 8/2002 | Bogoch et al. |
| 2002/0151677 A1 | 10/2002 | Bogoch et al. |
| 2003/0180328 A1 | 9/2003 | Bogoch et al. |
| 2003/0194414 A1 | 10/2003 | Bogoch et al. |
| 2003/0195874 A1 | 10/2003 | Akaboshi |
| 2005/0129715 A1 | 6/2005 | Paterson et al. |
| 2005/0271676 A1 | 12/2005 | Sette et al. |
| 2007/0128217 A1 | 6/2007 | ter Meulen et al. |

FOREIGN PATENT DOCUMENTS

| | | |
|---|---|---|
| DE | 3628658 A1 | 3/1988 |
| EP | 0 108 564 A1 | 5/1984 |
| IT | 98MI0874 | 10/1999 |
| JP | 3-503166 T | 7/1991 |
| JP | 8-287088 | 11/1996 |
| JP | 9121867 | 5/1997 |
| JP | 10-212300 A | 8/1998 |
| JP | 11001493 | 1/1999 |
| JP | 2000-253876 A | 9/2000 |
| KR | 10-1999-0008052 | 1/1999 |
| WO | 8907112 A1 | 8/1989 |
| WO | 96/32106 | 10/1996 |
| WO | 96/36436 | 11/1996 |
| WO | 0018351 A | 4/2000 |
| WO | 00/52054 | 9/2000 |
| WO | 0104135 A2 | 1/2001 |
| WO | 02085093 A2 | 10/2002 |
| WO | 0305880 A3 | 1/2003 |
| WO | 0383058 A2 | 10/2003 |
| WO | 200510032 A2 | 2/2005 |
| WO | 200504754 A2 | 11/2005 |

OTHER PUBLICATIONS

PCT International Search Report, PCT/US2002/09240, Jan. 14, 2004, USPTO, International Searching Authority, Washington DC.

(Continued)

*Primary Examiner* — Jason Sims
(74) *Attorney, Agent, or Firm* — Daren P. Nicholson

(57) ABSTRACT

A method and system are disclosed for identifying and/or locating complex patterns in an amino acid sequence stored in a computer file or database. According to an aspect of the present invention, techniques are provided to facilitate queries of protein databases. For protein descriptions received in response to the queries, embodiments of the present invention may scan the received protein descriptions to identify and locate Replikin patterns. A Replikin pattern is defined to be a sequence of 7 to about 50 amino acids that include the following three (3) characteristics, each of which may be recognized by an embodiment of the present invention: (1) the sequence has at least one lysine residue located six to ten amino acid residues from a second lysine residue; (2) the sequence has at least one histidine residue; and (3) at least 6% of the amino acids in the sequence are lysine residues.

11 Claims, 11 Drawing Sheets

OTHER PUBLICATIONS

PCT International Preliminary Examination Report, PCT/US2002/09240, Feb. 5, 2004, USPTO, International Preliminary Examination Authority, Alexandria, VA, USA.
PCT International Search Report, PCT/US2002/21494, May 30, 2003, USPTO, International Searching Authority, Washington DC.
PCT International Preliminary Examination Report, PCT/US2002/21494, Nov. 26, 2004, USPTO, International Searching Authority, Alexandria, VA, USA.
PCT International Search Report, PCT/US2003/08990, Dec. 7, 2005, International Searching Authority, USPTO, Alexandria, VA, USA.
PCT Written Opinion of the International Searching Authority, PCT/US2004/017936, Apr. 7, 2005, EPO, International Searching Authority, Munich, DE.
PCT International Search Report, PCT/US2004/017936, Apr. 28, 2005, EPO, International Searching Authority, Rijswijk, NL.
PCT International Preliminary Report on Patentability, PCT/US2004/017936, Apr. 13, 2007, USPTO, International Preliminary Examining Authority, Alexandria, VA, USA.
PCT International Search Report, PCT/US2005/014443, Oct. 21, 2005, EPO, International Searching Authority, Rijswijk, NL.
PCT Written Opinion of the International Searching Authority, PCT/US2005/014443, Apr. 12, 2006, EPO, International Searching Authority, Munich, DE.
PCT International Preliminary Report on Patentability, PCT/US2005/014443, Nov. 1, 2006, WIPO, International Bureau of WIPO, Geneva, Switzerland.
PCT International Search Report, PCT/US2006/05343, Sep. 25, 2007, USPTO, International Searching Authority, Alexandria, VA, USA.
Supplementary Partial European Search Report 99944002, Apr. 20, 2004, Munich, DE.
Supplementary Partial European Search Report 03721445.9, Dec. 12, 2006, EPO, International Searching Authority, Munich, DE.
NCBI accession # gi 75059 Jul. 16, 1999.
NCBI Listing JQ0032, May 11, 2000.
NCBI Accession # AAK38298, Apr. 19, 2001.
Abrams M. B. et al., "Early Detection and Monitoring of cancer with the Anti-Malignin Antibody Test," Cancer detection and Prevention, XX, XX, vol. 18, No. 1, 1994, pp. 65-78, XP000673180, ISSN:0361-090X.
Bogoch et al.: In vitro production of the general transformation antibody related to survival in human cancer patients; antimalignin antibody; Abstract, Cancer Detection and Prevention, 1988, vol. 12, Nos. 1-6, pp. 313-320. Database Medline on STN National Library of Medicine (Bethesda, MD, USA) No. 89028479.
Bogoch et al., "Aglyco Pathology of Viral Receptors in Dementias," Annals of the New York Academy of Sciences, New York Academy of Sciences, New York, NY, US, vol. 757, 1995, pp. 413-417, XP008003395, ISSN:0077-8923.
Bucher, D. et al., "M protein (M1) of influenza virus antigenic analysis and intracellular localization with monoclonal antibodies", J Virol. Sep. 1989; 63(9): pp. 3622-3633.
Keppeler et al., "Elongation of thr N-acyl side chain of sialic acid in MDCK II cells inhibits influenza A virus infection," abstract, Biochemical and Biophysical Research Communications, Dec. 18, 1998, vol. 253, No. 2. Database Medline on STN, National Library of Medicine, (Bethesda, MD, USA), No. 99097253.
Kornblith P. L. et al., "Growth-inhibitory effect of diphenylhydantoin on murine astrocytomas," Neurosurgery, vol. 5, No. 2, pp. 259-263 (Aug. 1979), MEDLINE, XP002199627.
Margalit et al., "Prediction of Immunodominant Helper T Cell Antigenic Sites From the Primary Sequence," Jour. Of Immunology, vol. 138, 2213-2229, Apr. 1, 1987.
Pannifer, Crystal structure of the anthrax lethal factor, Nature, vol. 414, pp. 229-233 (Nov. 2001).
Rodman, Toby C. et al., "Human Immunodeficiency Virus (HIV) Tat-reactive Antibodies Present in Normal HIV-negative Sera and Depleted in HIV-positive Sera. Identification of the Epitope," vol. 175, pp. 1247-1253, (May 1992).

Seal et al., "Elevation of Serum Protein-Bound Carbohydrates and Haptoglobin in Schizophrenia," Clinical Chemistry; Oct. 1996, vol. 12, No. 10, pp. 709-716.
Weber, E. et al., "Fine Mapping of a Peptide Sequence Containing an Antigenic Site Conserved Among Arenaviruses," Virology, vol. 164, p. 30-38 (1988).
Yasuko, A-O, et al., "Intranasal administration of adjuvant-combined recombinant influenza virus HA vaccine protects mice from the lethal H5N1 virus infection." Microbes and Infection, vol. 8, Issues 12-13, pp. 2706-2714, Oct. 2006.
Zhao, Neutralizing monoclonal antibody against Anthrax lethal factor inhibits intoxication in a mouse model, Human Antibodies, vol. 12, pp. 129-135 (2003).
Bogoch, S, et al. "Rapid replication and Replikintm structures: basis of the AMASRTest and CAVAXR." Cancer Detection and Prevention Online, Feb. 9, 2002, XP002350483.
Patil et al., "Identification of a Talin-binding Site in the Integrin β3 Subunit Distinct from the NPLY Regulatory Motif of a Post-ligand Binding Functions," The Journal of Biological Chemistry, vol. 274, No. 1, Oct. 1, 1999, p. 28575-28583.
Sharma et al., "Synthesis and Characterization of a Peptide Identified as a Functional element in αA-crystallin," The Journal of Biological Chemistry, vol. 275, No. 6, Feb. 11, 2000, p. 3767-3771.
Johansson et al., "Small, novel proteins from the mistletoe Pharadendron tementosum exhibit highly selective cytotoxicity to human breast cancer cells," Cell Mol. Life Sci, Jan. 2003, 60: 165-175.
PepBank entry 42800, corresponding to UniProt database entry P15516, Apr. 1, 1990 (Homo sapiens salival protein histatin), available at http://pepbank.mgh.harvard.edu, accessed Oct. 6, 2008.
PCT International Preliminary Report on Patentability, PCT/US2006/05343, Jul. 22, 2008, USPTO, International Preliminary Examining Authority, Alexandria, VA, USA.
EP Office Action 04785929.3, Sep. 1, 2008, EPO, Netherlands.
NZ Office Action 553983, Jul. 16, 2008, IPO, New Zealand.
Brumeanu, T.D. et al., "Immunogenicity of a Contiguous T-B Synthetic Epitope of the A/PR/8/34 Infuenza Virus," Journal of Virology, Jul. 1997, vol. 71, No. 7, pp. 5473-5480.
Chambers, T.M. et al., "Antigenic and molecular characterization of subtype H13 hemagglutinin of influenza virus," Database NCBI on STN, Accession Number HMIVT2, Virology, pp. 180-188, abstract, 1989, 172(1).
Gelder, CM et al. "Human CD4+ T-cell repertoire of response to influenza A virus hemagglutinin after recent natural infection, " Journal of Virology, Dec. 1995, vol. 69, No. 12, pp. 7497-7506A.
Bogoch, S, et al., "Rapid replication and Replikintm structures: basis of the AMASRTest and CAVAXR," Cancer Detection and Prevention Online, Feb. 9, 2002, XP002350483.
O'Donnell, F.T. et al., "Epidemiology and molecular characterization of co-circulating influenza A/H3N2 virus variants in children," Epidemiology and Infection, Jun. 2003, pp. 521-531, abstract, vol. 130, issue 3, The University of Texas-Houston School of Public Health, Houston, Texas.
Marra, M. et al., "The Genome Sequence of the SARS-Associated Coronavirus," Science, American Association for the Advancement of Science, US, v. 300, No. 5624, p. 1399-1404, XP002269483, ISSN: 0036-8075, May 30 2003.
Qin, E. et al., "A Genome Sequence of Novel SARS-CoV Isolates: the Genotype, GD-Ins29, Leads to a Hypothesis of Viral Transmission in South China," Genomics Proteomics & Bioinformatics, vol. 1, No. 2, p. 101-107, XP001206098, ISSN: 1672-0229, May 2003.
Bogoch, S. et al., "A Checklist for Suitability of Biomarkers as Surrogate Endpoints in Chemoprevention of Breast Cancer," Journal of Cellular Biochemistry, Supplement, Boston, US, vol. 19, pp. 173-185, XP009046492, ISSN: 0733-1959, 1994.
Shi et al., Immunogenicity and in vitro protective efficacy of a recombinant multistage Plasmodium falciparum candidate vaccine. Proc. Nat'l. Acad. Sci., USA. Feb. 1999, vol. 96, No. 4, pp. 1615-1620, see Table 1 and p. 1616, Materials and Methods.
Gao et al., Identification and characterization of T helper epitopes in the nucleoprotein of influenza A virus, J Immunol Nov. 1, 1989, vol.

143, No. 9, pp. 3007-3014, see Figure 1, first line, right hand side sequence (ERR . . .), 3008, col. 1, Viruses and Other Ag and Immunization.

Rota, P. et al., "Characterization of a Novel Coronavirus Associated with Severe Acute Respiratory Syndrome," Science, American Association for the Advancement of Science, US, v. 300, No. 5624, p. 1394-1399, XP002269482, ISSN: 0036-8075, May 30 2003.

Tanaka, T. et al., "Efficient Generation of Antibodies to Oncoproteins by using Synthetic Peptide Antigens." Proceedings of the National Academy of Sciences of USA, National Academy of Science, Washington, D.C., US, v. 82, No. 10, p. 3400-3404, tables 1, Peptide 21, XP000113798, ISSN: 0027-8424, May 1 1985.

Brown, L. R. et al., "Recognition of the influenza hemagglutinin by Class II MHC-restricted T lymphocytes and antibodies," Journal of Immunology, Oct. 15, 1991, pp. 2677-2684, vol. 147, No. 8, American Association of Immunologists, USA, XP002371257, ISSN: 0022-1767.

Atassi, M. Z. et al., "A novel approach for localization of the continuous protein antigenic sites by comprehensive synthetic surface scanning: Antibody and T cell activity to several influenza hemagglutinin synthetic sites," Immunological Communications, 1984, pp. 539-551, vol. 13, No. 6, Marcel Dekker, Inc., XP009062995, ISSN: 0090-0877.

Carr, C. M. et al., "A spring-loaded mechanism for the conformational change of influenza hemagglutinin," Cell, May 21, 1993, pp. 823-832, vol. 73, Cell Press, XP002059698, ISSN: 0092-8674.

Ben-Yedidia, T. et al., "Intranasal administration of peptide vaccine protects human/mouse radiation chimera from influenza infection," International Immunology, 1999, pp. 1043-1051, XP000914818, ISSN: 0953-8178.

Schenk, S. et al., "Four recombinant isoforms of Cor a 1, the major allergen of hazel pollen, show different reactivities with allergen-specific T-lymphocyte clones," European Journal of Biochemistry, 1994, pp. 717-722, vol. 224, XP002371408, ISSN: 0014-2956.

Orlando, C. et al., "A monoclonal antibody directed against the catalytic site of Bacillus anthracis adenylyl cyclase identifies a novel mammalian brain catalytic subunit," Biochemistry, 1992, pp. 3215-3222, vol. 31, American Chemical Society, XP002371438, ISSN: 0006-2960.

Japan Patent Office, Office Action in Japanese Application No. 2009-024307, dated Sep. 8, 2009 Japan.

United States Patent and Trademark Office, US Office Action in U.S. Appl. No. 11/615,578, dated Oct. 21, 2009, US.

NCBI Swiss-Prot Locus P33795, accessed Jul. 20, 2009.

Betakova et al., "The Vaccinia Virus A14.5L Gene Encodes a Hydrophobic 53-Amino-Acid Virion Membrane Protein That Enhances Virulence in Mice and Is Conserved among Vertebrate Poxviruses," Journal of Virology, vol. 74., No. 9, May 2000, p. 4085-4092.

Massung et al., "Potential virulence determinants in terminal regions of variola spallpox virus genome," Nature, vol. 366, Dec. 23/30, 1993, p. 748-751.

PCT International Search Report and Written Opinion, PCT/US2007/069978, Jun. 3, 2008, EPO, International Searching Authority, Rijswijk, NL.

PCT International Search Report and Written Opinion, PCT/US2007/82436, Jan. 9, 2009, USPTO International Searching Authority, Alexandria, VA, USA.

PCT International Search Report and Written Opinion, PCT/US2008/00645, Feb. 2, 2009, USPTO, International Searching Authority, Alexandria, VA, USA.

PCT International Search Report and Written Opinion, PCT/US2008/061336, Feb. 2, 2009, EPO, International Searching Authority, Rijswijk, NL.

EP Supplementary Search 02736514.7, Mar. 9, 2006.

EP Supplementary Search 02752202.8, Mar. 10, 2006.

Bogoch et al. "In vitro production of the general transformation antibody related to survival in human cancer patients: antimalignin antibody," Cancer Detection and Prevention, Sep. 28, 1988, vol. 12, Nos. 1-6, pp. 313-320.

Bogoch et al., "Replikins: The Chemistry of Rapid Replication," Begell House, Inc. NY, NY (2005).

Witteveldt, et al., "Protection of Penaeus monodon against White Spot Syndrome Virus by oral Vaccination," Journal of Virology, Feb. 2004, p. 2057-2061 vol. 78, No. 4, entire document, esp. p. 2060, col. 1.

PCT International Preliminary Report on Patentability, PCT/US2007/069978, May 1, 2009, USPTO, International Preliminary Examining Authority, Alexandria, VA, USA.

EP Office Action 04785929.3, Feb. 2, 2009, Netherlands.

NZ Office Action 560415, Mar. 6, 2009, IPO, New Zealand.

UnitProt/Swiss-Prot database entry O89746 1 Influenza A virus (strain A/Chicken/Hong Kong/220/1997 H5N1 genotype Gs/Gd) dated Nov. 1, 1998.

NCBI Accession No. AAW59548 (Jan. 24, 2005).

US Office Action, U.S. Appl. No. 11/755,597, mailed May 14, 2010.

SG Written Opinion, Application No. SG 200602419-4, mailed Aug. 3, 2010.

Rodriguez et al., "Plasmodium falciparum EBA-175 kDa protein peptides which bind to human red blood cells." Parasitology (2000), vol. 120, pp. 225-235.

US Office Action, U.S. Appl. No. 12/495,306, Sep. 1, 2010.

Fern, J. "Promiscuous malaria peptide epitope stimulates CD45Ra T cells from peripheral blood of nonexposed donors," J. Immunology 1992, vol. 148, pp. 907-913.

US Office Action, U.S. Appl. No. 12/108,458, Dec. 27, 2010.

US Office Action, U.S. Appl. No. 12/170,763, Feb. 15, 2011.

US Office Action, U.S. Appl. No. 12/252,028, Feb. 15, 2011.

US Office Action, U.S. Appl. No. 12/495,306, Feb. 15, 2011.

US Office Action, U.S. Appl. No. 12/010,027, Feb. 16, 2011.

US Office Action, U.S. Appl. No. 12/688,372, Mar. 28, 2011.

SG Written Opinion, Application No. SG 200602420-2, Apr. 6, 2011.

US Office Action, U.S. Appl. No. 12/789,877, Jun. 8, 2011.

EP Supplemental Search EP 10 01 2944, Apr. 20, 2011, EPO, Munich, DE.

EP Supplemental Search EP 10 01 2945.1, Jun. 6, 2011 EPO, Munich, DE.

US Notice of Allowance U.S. Appl. No. 11/923,559, Jun. 23, 2011.

CA Office Action, CA 2,441,540, Jul. 11, 2011, CIPO, CA.

CN Office Action, CN 200580012974, Jul. 19, 2011, CIPO, CN.

JP Office Action, JP 2007-555371, Jul. 12, 2011, JPO.

EP Partial Search Report, EP 11 158 084.1, Oct. 7, 2011, EPO.

EP Partial Search Report, EP 11 158 093.2, Oct. 14, 2011, EPO.

UniProt C2W513 (Jun. 16, 2009).

Buscaglia et al., "The repetitive domain of Trypanosoma cruzi trans-sialidase enhances the immune response against the catalytic domain," Journal of Infectious Diseases, University of Chicago Press, Chicago, IL, vol. 177, No. 2, Feb. 1, 1998, pp. 431-436.

Diggs et al. "Plasmodium falciparum: Passive immunization of Aotus lemurinus griselmembra with immune serum," Experimental Parasitology, vol. 80, Issue 2, Mar. 1995, pp. 291-296.

Ferro et al., "The androgen receptor CAG repeat: a modifier of carcinogenesis," Molecular and Cellular Endocrinology, 193, Jan. 1, 2002 , pp. 109-120.

Frankel et al., " Activity of synthetic peptides from the Tat protein of human immunodeficiency virus type 1," Proc. Natl. Acad. Sci.USA, Oct. 1989, vol. 86, pp. 7397-7401.

Guan et al., "Emergence of multiple genotypes of H5N1 avian influenza viruses in Hong Kong SAR," PNAS vol. 99, No. 13, Jun. 25, 2002, pp. 8950-8955.

He, Z. et al., "Identification of epitopes in cucumber mosaic virus using a phage-displayed random peptide library," J Gen Virol 1998, vol. 79, pp. 3145-3153 (accepted Aug. 21, 1998).

Kumar, et al., "Cytotoxic T Cells Specific for the Circumsporozoite Protein of Plasmodium Falciparum," Nature, vol. 334, Jul. 21, 1988, pp. 258-260, XP002027064.

Lal et al., "Identification of T-cell determinants in natural immune responses to the Plasmodium falciparum apical membrane antigen (AMA-1) in an adult population exposed to malaria," Infection and Immunity, vol. 64, No. 3, Mar. 1996, pp. 1054-1059, XP055000060.

Melville et al., "P58PK, a novel cochaperone containing tetratricopeptide repeats and a J-domain with oncogenic potential," Database accession No. PREV200000253165; & CMLS Cellular and Molecular Life Sciences, vol. 57, No. 2, Feb. 2000, pp. 311-322, ISSN: 1420-682X.

Ostroff, "Emerging infectious diseases 1997-1998: The role of molecular epidemiology," Memorias Do Instituto Oswaldo Cruz, vol. 94, No. 1, Jan. 1999, pp. 1-3, XP002636692.

Patarroyo et al., "Induction of protective immunity against experimental infection with malaria using synthetic peptides," Nature, vol. 328, No. 6131, Aug. 13, 1987, pp. 629-632.

Simeckova-Rosenberg et al., "Protection of mice against lethal viral infection by synthetic peptides corresponding to B- and T-cell recognition sites of influenza A hemagglutinin," VACCINE, vol. 13, No. 10, pp. 927-932 (1995).

Smith et al., "Finding sequence motifs in groups of functionally related proteins," PNAS, vol. 87, pp. 826-830, Jan. 1990.

Takahashi et al., "Antibody to Ras proteins in patients with colon cancer," Clin Cancer Res, Oct. 1995, vol. 1, pp. 1071-1077.

Wang et al., "ORF390 of white spot syndrome virus genome is identified as a novel anti-apoptosis gene," Biochemical and Biophysical Research Communications 325 (Nov. 2004) 899-907.

Yao et al., "Linear epitopes of sperm whale myoglobin identified by polyclonal antibody screening of random peptide library," Int J Peptide Protein Res, Jun. 30 1996, vol. 5, pp. 477-485.

NCBI Accession No. Np 740460, residues 201-210 (removed from NCBI) (2000).

3MOTIF—Search Instructions, 3motif in three Dimensions, article titles "Submitting a protein sequence": http://brutlag.stanford.edu/3motif/search_instr.html) (screenshot Apr. 27, 2005 in U.S. Appl. No. 11/116,203).

NCBI Blast Searching, Gene Gateway—Exploring Genes and Genetic Disorders, "Sequence similarity searching using NCBI Blast" (http:www.ORNL.gov/sci/techresources/Human_Genome/chromosome/blast.shtml) (Apr. 27, 2005).

NCBI Query Tutorial "Introduction" (http://www.ncbi.nim.nih.gov/Education/BLASTinfo/query_tutorial.html) (Apr. 27, 2005).

NCBI Query Tutorial "Introduction to a BLAST Query" (http://www.ncbi.nim.nih.gov/Education/BLASTinfo/tut1.html) (Apr. 27, 2005).

NCBI Query Tutorial "Setting up a BLAST Search" (http://www.ncbi.nim.nih.gov/Education/BLASTinfo/Blast_setup.html) (Apr. 27, 2005).

Kazazic et al., "Mutational analysis of the role of charged residues in target-cell binding, potency and specificity of the pediocin-like bacteriocin sakacin P," Microbiology, (Jul. 2002) 148: 2019-27.

U.S. Office Action, U.S. Appl. No. 12/688,372, Nov. 21, 2011, USPTO.

KR Office Action, KR 10-2006-7021152, Dec. 8, 2011, KIPO.

JP Office Action, JP 2007-510929, Aug. 30, 2011, JPO.

NCBI Accession No. NP_052803 (May 14, 1998).

ACML 01000595 database entry (May 1, 2009).

Cross et al., "Studies on influenza haemagglutinin fusion peptide mutants generated by reverse genetics," The EMBO Journal vol. 20 No. 16 pp. 4432-4442, 2001.

Okuno et al., "A Common Neutralizing Epitope Conserved between the Hemagglutinins of Influenza a Virus H1 and H2 Strains," Journal of Virology, vol. 67, No. 5, May 1993, p. 2552-2558.

| Amino Acid | Abbreviation | Code |
|---|---|---|
| Alanine | Ala | a |
| Arginine | Arg | r |
| Asparagine | Asn | n |
| Aspartic acid | Asp | d |
| Cysteine | Cys | c |
| Glutamine | Glu | q |
| Glutamic acid | Gln | e |
| Glycine | Gly | g |
| Histidine | His | h |
| Isoleucine | Ile | i |
| Leucine | Leu | l |
| Lysine | Lys | k |
| Methionine | Met | m |
| Phenylalanine | Phe | f |
| Proline | Pro | p |
| Serine | Ser | s |
| Threonine | Thr | t |
| Tryptophan | Trp | w |
| Tyrosine | Tyr | y |
| Valine | Val | v |

FIG. 1: Amino Acid Encoding.

```
1: AAF04328. serine protease D...[gi:6137097]  BLink, Links

LOCUS       AAF04328                 422 aa            linear   PRI 20-APR-2004
DEFINITION  serine protease DESC1 [Homo sapiens].
ACCESSION   AAF04328
VERSION     AAF04328.1  GI:6137097
DBSOURCE    accession AF064819.1
KEYWORDS
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (residues 1 to 422)
  AUTHORS   Lang,J.C. and Schuller,D.E.
  TITLE     Differential expression of a novel serine protease homologue in
            squamous cell carcinoma of the head and neck
  JOURNAL   Br. J. Cancer 84 (2), 237-243 (2001)
   MEDLINE   21094880
   PUBMED    11161383
REFERENCE   2  (residues 1 to 422)
  AUTHORS   Lang,J.C. and Schuller,D.E.
  TITLE     Direct Submission
  JOURNAL   Submitted (12-MAY-1998) Otolaryngology, Ohio State University, 1248
            James Cancer Hospital, 300 West 10th Avenue, Columbus, OH 43210,
            USA
COMMENT     Method: conceptual translation.
FEATURES             Location/Qualifiers
     source          1..422
                     /organism="Homo sapiens"
                     /db_xref="taxon:9606"
                     /chromosome="4"
                     /map="4q12-q13; between D4S1619 and WI-7844; 20.21 cR from
                     WI-5548"
     Protein         1..422
                     /product="serine protease DESC1"
                     /name="expressed in normal oral epithelium, but not in
                     squamous cell tongue carcinoma or metastatic neck nodal
                     tissue"
     Site            167
                     /site_type="cleavage"
                     /note="between arginine and isoleucine"
     Site            208
                     /site_type="active"
                     /note="histidine; part of the catalytic triad"
     Site            253
                     /site_type="active"
                     /note="aspartic acid; part of the catalytic triad"
     Site            349
                     /site_type="active"
                     /note="serine; part of the catalytic triad"
     CDS             1..422
                     /gene="DESC1"
                     /coded_by="AF064819.1:56..1324"
ORIGIN
        1 myrpdvvrar krvcwepwvi glvifisliv lavcigltvh yvrynqkkty nyystlsftt
       61 dklyaefgre asnnftemsq rlesmvknaf yksplreefv ksqvikfsqq khgvlahmll
      121 icrfhstedp etvdkivqlv lheklqdavg ppkvdphsvk ikkinktetd sylnhccgtr
      181 rsktlgqslr ivggteveeg ewpwqaslqw dgshrcgatl inatwlvsaa hcfttyknpa
      241 rwtasfgvti kpskmkrglr riivhekykh pshdydisla elsspvpytn avhrvclpda
      301 syefqpgdvm fvtgfgalkn dgysqnhlrq aqvtlidatt cnepqaynda itprmlcags
      361 legktdacqg dsggplvssd ardiwylagi vswgdecakp nkpgvytrvt alrdwitskt
      421 gi
//
```

FIG. 2: Cancer Protein Description.

| Nucleic Acid Base Triplets | Corresponding Amino Acid | Code |
|---|---|---|
| GCT GCC GCA GCG | Alanine | a |
| CGT CGC CGA CGG AGA AGG | Arginine | r |
| AAT AAC | Asparagine | n |
| GAT GAC | Aspartic acid | d |
| TGT TGC | Cysteine | c |
| CAA CAG | Glutamine | q |
| GAA GAG | Glutamic acid | e |
| GGT GGC GGA GGG | Glycine | g |
| CAT CAC | Histidine | h |
| ATT ATC ATA | Isoleucine | i |
| TTG TTA CTT CTC CTA CTG | Leucine | l |
| AAA AAG | Lysine | k |
| ATG | Methionine | m |
| TTT TTC | Phenylalanine | f |
| CCT CCC CCA CCG | Proline | p |
| TCT TCC TCA TCG AGT AGC | Serine | s |
| ACT ACC ACA ACG | Threonine | t |
| TGG | Tryptophan | w |
| TAT TAC | Tyrosine | y |
| GTT GTC GTA GTG | Valine | v |
| TAA TAG TGA | < stop code > | |
| | | |

FIG. 3: Nucleic Acid Base – Amino Acid Correspondence.

FIG. 4: Increasing Replikin Concentration ("Replikin Count") of Hemagglutinin Protein of H5N1 Prior to Three 'Bird Flu' Epidemics.

| Category | SEQ. ID. | Name | Replikin Pattern |
|---|---|---|---|
| Bacteria: | 10 | Mycoplasma pulmonic, chromosome replication | kkektthnk |
| | 43 | Macrophage infectivity potentiator, L. legionella | kvhffqlkk |
| Tumor Viruses: | 48 | Rous sarcoma virus tyrosine-protein kinase | kklrhek |
| | 49 | v-yes, avian sarcoma | kklrhdk |
| | 50 | c-yes, colon cancer, malignant melanoma | kklrhdk |
| | 51 | v-srcC, avian sarcoma | kklrhek |
| | 52 | c-src, colon, mammary, panrcreatic cancer | kklrhek |
| | 53 | Neuroblastoma RAS viral (v-ras) oncogene | kqahelak |
| | 54 | VPl (major capsid protein) [Polyamavirus sp.] | kthrfskh |
| | 55 | Sindbis | knlhekik |
| | 56 | El [Human papilloamavirus type 71] | khrpllqlk |
| | 57 | v-erbB from AEV and c-erb | kspnhvk |
| | 58 | v-fms (feline sarcoma) | knihlekk |
| | 59 | c-fms (acute and chronic myelomonocytic tumors) | knihlekk |
| | 60 | large t-antigen I [Polyomavirus sp.l | kphlaqslek |
| | 61 | middle t-antigen [Polyomavirus sp,l- | kqhrelkdk |
| | 62 | small t-antigen [Polyomavirus spJ, | kqhrelkdk |
| | 63 | v-abl, murine acute leukemia | kvpvlisptlkh |
| | 64 | Human T-cell lymphotropic virus typo 2 | ksillevdkdish |
| | 65 | c-kit, GI tumors, small cell lung carcinoma | kagitimvkreyh |
| | 18 | Hepatitis C | hyppkpgcivpak |
| Trans-forming Proteins: | 66 | Transforming protein myb | ksgkhlgk |
| | 67 | Transforming protein myc, Burkitt lymphoma | krreqlkhk |
| | 68 | Ras-related GTP-binding protein | ksfevikvih |
| | 69 | Transforming protein ras (teratocarcinoma) | kkkhtvkk |
| | 70 | TRAF-associated NF●kB activator TANK | kaqkdhlsk |
| | 71 | RFP transforming protein | hlkrvkdlkk |
| | 72 | Transforming protein D (S.C.) | kygspkhrlik |
| | 73 | Papilloma virus type 11, transforming protein | klkhilgkarfik |
| | 74 | Protein tryosine kinasc (EC 2.7.1.ll2slk | kgdhvkhykirk |
| | 75 | Transforming protein (axl(-)) | keklrdvmvdrhk |
| | 76 | Transforming protein (N-myc) | klqarqqqllkkieh |
| | 77 | Fibroblast growth factor 4 (Kaposi sarcoma) | kkgnrvsptmkvth |
| Cancer Cell Proteins: | 78 | Matrix metaloproteinase 7 (uterine) | keiplhfrk |
| | 79 | Transcription factor 7-like | kkkphikk |
| | 80 | Breast cancer antigen NY-BR-87 | ktrhdplak |
| | 81 | BRCA-1-Associated Ring Domain Protein (breast) | khhpkdnlik |
| | 82 | Autoantigen from a breast tumor' | khkrkkfrqk |
| | 83 | Glioma Replikin (this study) | kagvaflhkk |
| | 84 | Ovarian cancer antigen | khkrkkfrqk |
| | 85 | EE L leukemia | kkkskkhkdk |
| | 86 | Proto-oncogene tyrosine-protein kinase C-ABLE | hksekpalprk |
| | 87 | Adenomatosis polyposis coli | kkkkpsrlkgdnek |
| | 88 | Gastric cancer transforming protein | ktkkgnrvsptmkvth |
| | 89 | Transforming protein (K-RAS 2B),lung | khkekmskdgkkkkkksk |

FIG. 5 Selected examples of Replikins in various organisms.

700

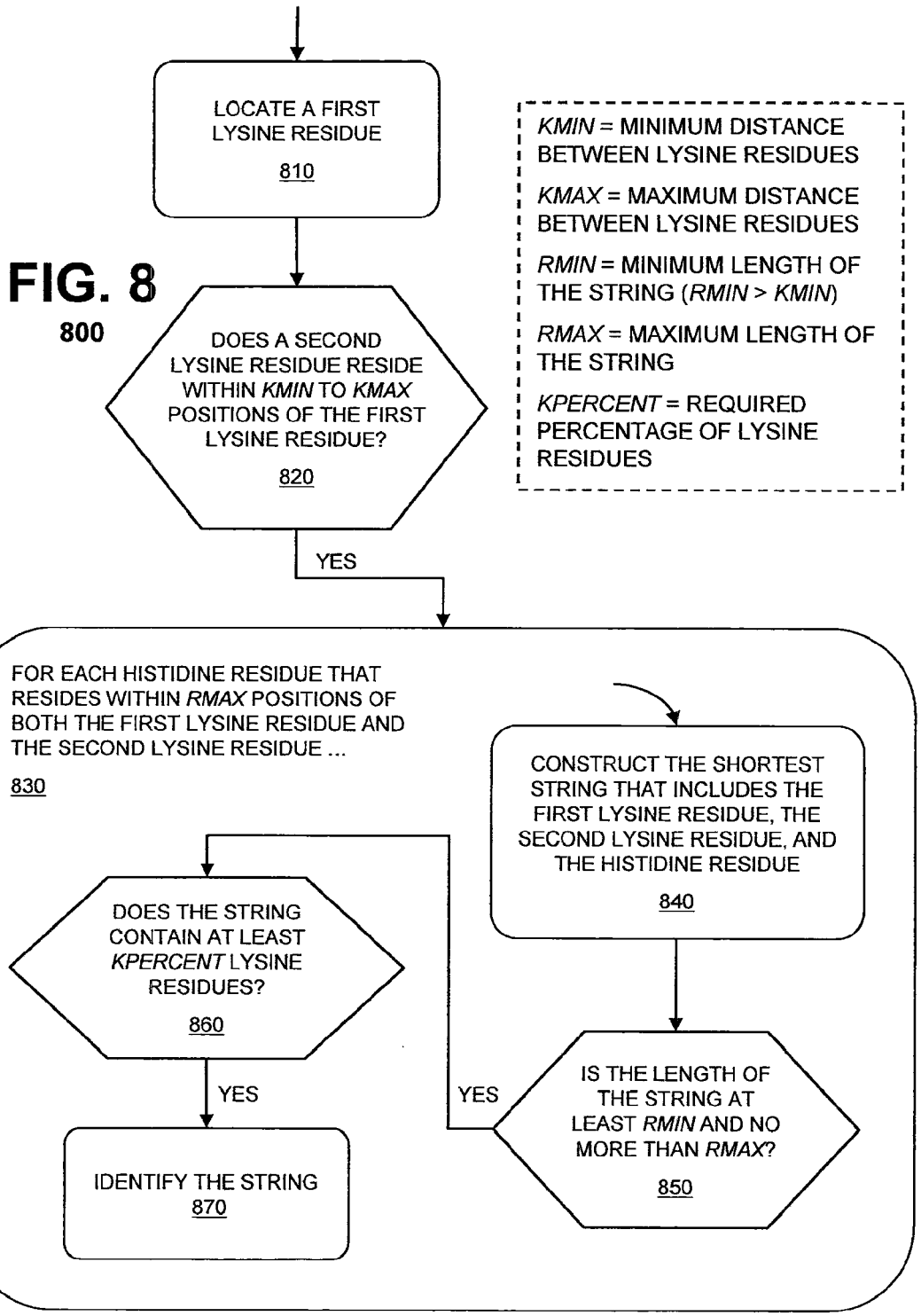

```

#   Discover a subsequence h...k...k, k...h...k, or k...k...h such that
#   (1) The distance between ks is in the range kmin..kmax.
#   (2) The distance between an h and the farthest k is in the range kmin+1..hmax.
#   (3) The fraction of k in the subsequence is percent or larger.

#   The sequence is searched for all possible subsequences that match,
#   and all these subsequences are returned.

set kmin 6; set kmax 10
set hmax 50
set percent 6 proc match {sequence} {
    global kmin kmax hmax percent set pos 0
    set L {}
    array set F {}
    foreach e [regexp -all -indices -inline k $sequence] {
        lappend L [lindex $e 0]
    } for {set i 1} {$i<[llength $L]} {incr i} {
        set k0 [lindex $L [expr {$i-1}]]

#  rule 1.
        for {set j $i; set wideenough 0} {!$wideenough && $j<[llength $L]} {incr j} {
            set k1 [lindex $L $j]
            if {$k1-$k0<$kmin} continue
            if {$k1-$k0>$kmax} break rule 2.
            set offset [expr $k1-$hmax]
            if {$offset<0} {set offset 0}
            while 1 {
                set h [string first h $sequence $offset]
                if {$h<0 || $h>$k0+$hmax} break
                if {$h<$k0} {
                    set b $h
                } else {
                    set b $k0
                }
                if {$h>$k1} {
                    set e $h
                } else {
                    set e $k1
                } rule 3.
                set subsequence [string range $sequence $b $e]
                set nk [regexp -all k $subsequence]
                if {double($nk)/double([string length $subsequence])*100>=$percent} {
                    set "F($b $e)" 1
                } incr offset
            }
        }
    }
    lsort -integer -index 0 [array names F]
}
```

FIG. 9 Replikin Matching Code.

```
1234....................29
+---------------------------+
kkgtsypklsksytnnkgkevlvlwgvhh      1917        H1N_  Influenza Goose Replikin
kkgssypklsksytnnkgkevlvlwgvhh      1918        H1N1  Human Influenza Pandemic
kkensypklsksyynnkgkevlvlwgvhh      1930        H1N1
kkgqsypklgksygnnkgkevlvlwgvhh      1933        H0N1
kkgtsypklsksytnnkgkevlvlwgvhh      1976        H1N1
kkgtsypklsksytnnkgkevlvlwgvhh      1977        H1N1
kkgnsypklsksytnnkgkevlv wgvhh      1979        H1N1
kkgnsypklsksytnnkgkevlv wgvhh      1980        H1N1
kkgtsypklsksytnnkgkevlvlwgvhh      1980        H1N1
kkgnsypklsksytnnkgkevlv wgvhh      1981        H1N1
kkgtsypklsksytnnkgkevlvlwgvhh      1981        H1N1
kkgtsypklsksytnnkgkevlvlwgvhh      1985        H1N1
kkgnsypklsksytnnkgkevlv wgvhh      1991        H1N1
kkgnsypklsksytnnkgkevlv wgvhh      1992        H1N1
kkgnsypklsksytnnkgkevlv wgvhh      1996        H1N1
kkgnsypklsksytnnkgkevlv wgvhh      1996        H1N1
kkgssypklsksyynnkgkevlvlwgvhh      1997        H1N1
kkgssypklsksyynnkgkevlvlwgvhh      1998        H1N1
kkgnsypklsksytnnkgkevlv wgvhh      1999        H1N1
kkgnsypklsksytnnkgkevlv wgvhh      2000        H1N1
kkgnsypklsksytnnkgkevlv wgvhh      2001        H1N1
kkgnsypklsksytnnkgkevlv wgvhh      2002        H1N1
kkgnsypklsksynnnkekevlvlwgshh      1999        H1N2  Influenza
kkgnsypklsksynnkkkevlv wgshh       2000        H1N2
kkgnsypklsksynnkgkevlvlwgshh       2001        H1N2
kkgtsypklsksytnnkkkevlvlwgvhh-     2001        H1N2
-knneypnlsksynnkekevlvlwgvhh       2002        H1N2
-knneypnlsksynnkekevlvlwgvhh       2002        H1N2
kkensypklgksennkeklv wgihh         1968        H3N2  Human Influenza Pandemic
----------ksynneegdlewgihh         1979-2003   H7N7  Influenza
kkgpnypvaesynneggmle wgvhh         1957        H2N2  Human Influenza Pandemic
kkgpnypvaesynneggmle wgihh         1957        H2N2  Human Influenza Pandemic
kkrneypeklsynneedilvlwgihh         2002        H5N2  Influenza
kkrneypeklsysnneedilvlwgihh        1959        H5N1  Influenza (Scotland)
kknneypekisynneedilvlwgihh         1975        H5N1  (Wisconsin)
kknneypekisynneedilvlwgihh         1981        H5N1  (Minnesota)
kkgneypekisynneedilvlwgihh         1983        H5N1  (Pennsylvania)
kkrneypekisynneedilvlwgihh         1988        H5N1  (Scotland)
kkrneypekisynneedilvlwgihh         1996        H5N1  (China)
kkrneypekisynneedilvlwgihh         1997        H5N1  (China)
kkrneypekisynneedilvlwgihh         1998        H5N1  (China)
kkrneypekisynneedilvlwgihh         1999        H5N1  (China)
kkrneypekisynneedilvlwgihh         2000        H5N1  (China)
kkrneypekisynneedilvlwgihh         2001        H5N1  (China)
kkrneypekisynneedilvlwgihh         2001        H5N1  (China)
kkrneypekisynneedilvlwgihh         2002        H5N1  (China)
kkrneypekisynneedilvlwgihh         2002        H5N1  (Thailand)
kkrneypekisynneedilvlwgihh         2002        H5N1  (Vietnam)
kkrneypekisynneedilvlwgihh         2003        H5N1  (Vietnam)
kkrneypekisynneedilvlwgihh         2003        H5N1  (Thailand)
kkrneypekisynneedilvlwgihh         2003        H5N1  (Sindong, China)
kkrneypekisynneedilvlwgihh         2003        H5N1  (China)
kkrneypekisynneedilv wgihh         2004        H5N1  (Vietnam, highly pathogenic)
kkrneypekisynneedilvlwgihh         2004        H5N1  (Vietnam,"highly pathogenic",gull)
kkrneypekisynneedilvlwgihh         2004        H5N1  (Vietnam, highly pathogenic)
kkrneypekisynneedilvlwgihh         2004        H5N1  (Thailand, highly pathogenic)
kkrneypekisynneedilvlwgihh         2004        H5N1  (Thailand, highly pathogenic)
kkrneypekisynneedilvlwgihh         2004        H5N1  (China,highlypathogenic)
kkrneypeklsxnneedilvlwgihh         2004        H5N1  (China,"highly pathogenic", goose)
```

FIG. 10 Replikin Scaffolding.

**Residues identical to the original 1917 Goose Replikin residues are not highlighted.
Amino acid substitutions are highlighted. Scaffolding is shown in Boldface.**

1100

SYSTEM AND METHOD FOR IDENTIFYING COMPLEX PATTERNS OF AMINO ACIDS

RELATED APPLICATIONS

This application is a Continuation of U.S. application Ser. No. 11/116,203, filed Apr. 28, 2005 and entitled "SYSTEM AND METHOD FOR IDENTIFYING COMPLEX PATTERNS OF AMINO ACIDS," which claims priority under 35 U.S.C. §119(e) from U.S. Provisional Patent Application Ser. No. 60/565,847, filed Apr. 28, 2004 and entitled "SYSTEM AND METHOD FOR IDENTIFYING COMPLEX PATTERNS OF AMINO ACIDS." and U.S. Provisional Patent Application Ser. No. 60/653,083, filed Feb. 16, 2005 and entitled "SYSTEM AND METHOD FOR IDENTIFYING COMPLEX PATTERNS OF AMINO ACIDS." Both of these provisional applications are incorporated herein by reference in their entireties and for all purposes.

Additionally, application Ser. No. 11/116,203 claims priority from and is a Continuation In Part of U.S. Non-provisional patent application Ser. No. 10/189,437, entitled "REPLIKIN PEPTIDES AND USES THEREOF," filed Jul. 8, 2002, now U.S. Pat. No. 7,452,963, which is a Continuation In Part of U.S. Non-provisional patent application Ser. No. 10/105,232, entitled "REPLIKIN PEPTIDES IN RAPID REPLICATION OF GLIOMA CELLS AND IN INFLUENZA EPIDEMICS," filed Mar. 26, 2002, now U.S. Pat. No. 7,189,800, which is a Continuation In Part of U.S. Non-provisional patent application Ser. No. 09/984,057, entitled "REPLIKINS AND METHODS OF IDENTIFYING REPLIKIN-CONTAINING SEQUENCES," filed Oct. 26, 2001, now U.S. Pat. No. 7,420,028. Further, application Ser. No. 11/116,203 claims priority from and is a Continuation In Part of U.S. Non-provisional patent application Ser. No. 10/860,050, entitled "REPLIKIN PEPTIDES AND USES THEREOF," filed Jun. 4, 2004, now U.S. Pat. No. 7,442,761. All of these non-provisional applications are incorporated herein by reference in their entireties and for all purposes.

TECHNICAL FIELD

This invention relates generally to the field of bioinformatics. More particularly, the invention relates to techniques for facilitating the identification of complex patterns of nucleotide or amino acid sequences.

BACKGROUND OF THE INVENTION

As is well-known, amino acids are the building blocks of proteins. Proteins make up the bulk of cellular structures, and some proteins serve as enzymes for facilitating cellular reactions. Twenty different amino acids are known to occur in proteins. The properties of each protein are dictated in part by the precise sequence of component amino acids.

Databases of amino acids and proteins are maintained by a variety of research organizations, including, for example, the National Center for Biotechnology Information (NCBI) at the U.S. National Library of Medicine, and the Influenza Sequence Database at the Los Alamos National Laboratory. These databases are typically accessible via the Internet through web pages that provide a researcher with capabilities to search for and retrieve specific proteins. These databases may also be accessible to researchers via local-area and wide-area networks. Additionally, researchers may directly access amino acid and protein databases stored on peripheral devices, such as magnetic disks, optical disks, static memory devices, and a variety of other digital storage media known in the art.

In amino acid and protein databases, amino acids are typically encoded as alphabetic characters. FIG. 1 lists each amino acid known to occur in proteins and provides a typical 3-letter abbreviation and single-letter code by which the amino acids may be represented in databases, according to a standard supplied by the International Union of Pure and Applied Chemistry (IUPAC).

A given protein may be described by its sequence of amino acids. For example, using the single-letter code given in FIG. 1, the character string "crvpsgvdla" corresponds to the protein defined by the following sequence of amino acids: cysteine, arginine, valine, proline, serine, glycine, valine, aspartic acid, leucine, and alanine.

When a protein database is searched for proteins that satisfy certain criteria (for example, those proteins relating to cancer in humans), the protein database search engine may respond by identifying hundreds or thousands of matching proteins. This set of matching proteins may be narrowed by supplying additional search criteria. At any point during the search process, specific proteins may be selected and reviewed. In FIG. 2, a printout describes a specific protein identified from an NCBI search for proteins relating to human cancer.

As can be seen in FIG. 2, a protein description may include detailed information describing, among other identifying factors, such information as the title of the protein ("Differential expression of a novel serine protease homologue in squamous cell carcinoma of the head and neck"), the authors of the protein description ("Lang, J. C. and Schuller, D. E."), and the organism from which the protein was isolated ("Homo sapiens").

Protein descriptions may include a specific sequence of amino acids that define the protein. For example, in FIG. 2, amino acid sequence data is found at the end of the description of the protein, in a section of the printout prefaced by the word "ORIGIN." In this example, the first few amino acids are "myrpdvvrar," which correspond to methionine, tyrosine, arginine, proline, aspartic acid, valine, valine, arginine, alanine, and arginine.

Some protein descriptions may include a sequence of nucleic acid bases, rather than amino acid sequences, that define the protein. As is known, a sequence of three nucleic acid bases (i.e., a nucleic acid base triplet) may correspond to an amino acid according to a mapping provided by the table found in FIG. 3. Each nucleic acid base triplet identified in the table represents or corresponds to a specific amino acid. For example, the nucleic acid triplet GCT (guanine-cytosine-thymine) corresponds to the amino acid Alanine. Similarly, the nucleic acid triplet GCA (guanine-cytosine-adenine) also corresponds to the amino acid Alanine. As another example, the nucleic acid triplets AAA and AAG (adenine-adenine-adenine and adenine-adenine-guanine, respectively) each corresponds to the amino acid Lysine.

The Replikin Pattern

In previous patent applications, the inventors have identified and described a pattern of amino acids that has been designated a "Replikin pattern" or simply a "Replikin." A Replikin pattern comprises a sequence of about 7 to about 50 contiguous amino acids that includes the following three (3) characteristics:

(1) the sequence has at least one lysine residue located six to ten amino acid residues from a second lysine residue;

(2) the sequence has at least one histidine residue; and (3) the sequence has at least 6% lysine residues.

Replikins have been shown to be associated with rapid replication in fungi, yeast, viruses, bacteria, algae, and cancer cells. Based on this association, it is believed that Replikins may be an indicator of disease. Additionally, an increase in concentration of Replikins over time may be an indicator of the imminent onset of disease. For example, before each of the three influenza pandemics of the last century (identified as H1N1, H2N2 and H3N2), there was a significant increase in the concentration of Replikins in the corresponding influenza virus. With respect to the H5N1 influenza, FIG. 4 illustrates a rapid increase in the concentration of Replikins per 100 amino acids just prior to epidemics in 1997 (indicated as E1), 2001 (indicated as E2) and 2004 (indicated as E3). Replikin patterns have been found in a variety of disease-related proteins, including cancers of the lung, brain, liver, soft-tissue, salivary gland, nasopharynx, esophagus, stomach, colon, rectum, gallbladder, breast, prostate, uterus, cervix, bladder, eye, forms of melanoma, lymphoma, leukemia, and kidney. Importantly, Replikin patterns appear to be absent from the normal healthy human genome. FIG. 5 lists selected examples of Replikin patterns that have been found in various organisms.

For example, the 13-residue pattern "hyppkpgcivpak," occurring in Hepatitis C (which is the last entry in the Tumor Virus Category of FIG. 5) is a Replikin pattern because: (1) it contains two lysine residues that are 8 positions apart; (2) it contains a histidine residue; and (3) the percentage of lysine residues is 2/13, which is 15.4%.

Amino Acid Search Tools

As is known in the art, databases of proteins and amino acids may be searched using a variety of database tools and search engines. Using these publicly available tools, patterns of amino acids may be described and located in many different proteins corresponding to many different organisms. Several methods and techniques are available by which patterns of amino acids may be described. One popular format is the PROSITE pattern. A PROSITE pattern description may be assembled according to the following rules:

(1) The standard International Union of Pure and Applied Chemistry (IUPAC) one-letter codes for the amino acids are used (see FIG. 1).

(2) The symbol 'x' is used for a position where any amino acid is accepted.

(3) Ambiguities are indicated by listing the acceptable amino acids for a given position, between square parentheses '[ ]'. For example: [ALT] would stand for Alanine or Leucine or Threonine.

(4) Ambiguities are also indicated by listing between a pair of curly brackets '{ }' the amino acids that are not accepted at a given position. For example: {AM} stands for any amino acid except Alanine and Methionine.

(5) Each element in a pattern is separated from its neighbor by a '-'.

(6) Repetition of an element of the pattern can be indicated by following that element with a numerical value or a numerical range between parenthesis. Examples: x(3) corresponds to x-x-x, x(2,4) corresponds to x-x or x-x-x or x-x-x-x.

(7) When a pattern is restricted to either the N- or C-terminal of a sequence, that pattern either starts with a '<' symbol or respectively ends with a '>' symbol.

(8) A period ends the pattern.

Examples of PROSITE patterns include:

PA [AC]-x-V-x(4)-{ED}. This pattern is translated as: [Alanine or Cysteine]-any-Valine-any-any-any-any-{any but Glutamic Acid or Aspartic Acid}

PA <A-x-[ST](2)-x(0,1)-V. This pattern, which must be in the N-terminal of the sequence ('<'), is translated as: Alanine-any-[Serine or Threonine]-[Serine or Threonine]-(any or none)-Valine.

Another popular format for describing amino acid sequence patterns is the regular expression format that is familiar to computer scientists. In computer science, regular expressions are typically used to describe patterns of characters for which finite automata can be automatically constructed to recognize tokens in a language. Possibly the most notable regular expression search tool is the Unix utility grep.

In the context of describing amino acid sequence patterns, a simplified set of regular expression capabilities is typically employed. Amino acid sequence patterns defined by these simple regular expression rules end up looking quite similar to PROSITE patterns, both in appearance and in result. A regular expression description for an amino acid sequence may be created according to the following rules:

(1) Use capital letters for amino acid residues and put a "-" between two amino acids (not required).

(2) Use "[ . . . ]" for a choice of multiple amino acids in a particular position. [LIVM] means that any one of the amino acids L, I, V, or M can be in that position.

(3) Use "{ . . . }" to exclude amino acids. Thus, {CF} means C and F should not be in that particular position. In some systems, the exclusion capability can be specified with a "^" character. For example, AG would represent all amino acids except Glycine, and [^ILMV] would represents all amino acids except I, L, M, and V.

(4) Use "x" or "X" for a position that can be any amino acid.

(5) Use "(n)", where n is a number, for multiple positions. For example, x(3) is the same as "xxx".

(6) Use "(n1,n2)" for multiple or variable positions. Thus, x(1,4) represents "x" or "xx" or "xxx" or "xxxx".

(7) Use the symbol ">" at the beginning or end of the pattern to require the pattern to match the N or C terminus. For example, ">MDEL" finds only sequences that start with MDEL. "DEL>" finds only sequences that end with DEL.

The regular expression, "[LIVM]-[VIC]-x(2)-G-[DENQTA]-x-[GAC]-x(2)-[LIVMFY](4)-x (2)-G" illustrates a 17 amino acid peptide that has: an L, I, V, or M at position 1; a V, I, or C at position 2; any residue at positions 3 and 4; a G at position 5 and so on . . . .

Other similar formats are in use as well. For example, the Basic Local Alignment Search Tool (BLAST) is a well-known system available on the Internet, which provides tools for rapid searching of nucleotide and protein databases. BLAST accepts input sequences in three formats: FASTA sequence format, NCBI Accession numbers, or GenBank sequence numbers. However, these formats are even more simple in structure than regular expressions or PROSITE patterns. An example sequence in FASTA format is:

```
>gi|532319|pir|TVFV2E|TVFV2E envelope protein
ELRLRYCAPAGFALLKCNDADYDGFKTNCSNVSVVHCTNLMNTTVTTGLL

LNGSYSENRTQIWQKHRTSNDSALILLNKHYNLTVTCKRPGNKTVLPVTI

MAGLVFHSQKYNLRLRQAWCHFPSNWKGAWKEVKEEIVNLPKERYRGTND

PKRIFFQRQWGDPETANLWFNCHGEFFYCKMDWFLNYLNNLTVDADHNEC

KNTSGTKSGNKRAPGPCVQRTYVACHIRSVIIWLETISKKTYAPPREGHL

ECTSTVTGMTVELNYIPKNRTNVTLSPQIESIWAAELDRYKLVEITPIGF

APTEVRRYTGGHERQKRVPFVXXXXXXXXXXXXXXXXXXXXXXVQSQHLL

AGILQQQKNLLAAVEAQQQMLKLTIWGVK
```

Features of the BLAST system include sequence comparison algorithms that are used to search sequence databases for regions of local alignments in order to detect relationships among sequences which share regions of similarity. However, the BLAST tools are limited in terms of the structure of amino acid sequences that can be discovered and located. For example, BLAST is not capable of searching for a sequence that has "at least one lysine residue located six to ten amino acid residues from a second lysine residue," as required by a Replikin pattern, for example. Nor is BLAST capable of searching for amino acid sequences that contain a specified percentage or concentration of a particular amino acid, such as a sequence that has "at least 6% lysine residues."

Need for Replikin Search Tools

As can be seen from its definition, a Replikin pattern description cannot be represented as a single linear sequence of amino acids. Thus, PROSITE patterns and regular expressions, both of which are well suited to describing ordered strings obtained by following logical set-constructive operations such as negation, union and concatenation, are inadequate for describing Replikin patterns.

In contrast to linear sequences of amino acids, a Replikin pattern is characterized by attributes of amino acids that transcend simple contiguous ordering. In particular, the requirement that a Replikin pattern contain at least 6% lysine residues, without more, means that the actual placement of lysine residues in a Replikin pattern is relatively unrestricted. Thus, in general, it is not possible to represent a Replikin pattern description using a single PROSITE pattern or a single regular expression.

Accordingly, there is a need in the art for a system and method to scan a given amino acid sequence and identify all instances of a Replikin pattern. Similarly, there is a need in the art for a system and method to search protein databases and amino acid databases for amino acid sequences that match a Replikin pattern. Additionally, there is a need in the art for a generalized search tool that permits researchers to locate amino acid sequences of arbitrary specified length that includes any desired combination of the following characteristics: (1) a first amino acid residue located more than N positions and less than M positions away from a second amino acid residue; (2) a third amino acid residue located anywhere in the sequence; and (3) the sequence contains at least R percent of a fourth amino acid residue. Finally, the shortcomings of the prior art are even more evident in research areas relating to disease prediction and treatment. There is a significant need in the art for a system to predict in advance the occurrence of disease (for example, to predict strain-specific influenza epidemics) and similarly to enable synthetic vaccines to be designed based on amino acid sequences or amino acid motifs that are discovered to be conserved over time and which have not been previously detectable by prior art methods of searching proteins and amino acid sequences.

BRIEF DESCRIPTION OF THE DRAWINGS

FIG. 1 is a conversion table that enables amino acids to be encoded as single alphabetic characters according to a standard supplied by the International Union of Pure and Applied Chemistry (IUPAC).

FIG. 2 is a printout of a human cancer protein obtained by searching a protein database maintained by the National Center for Biotechnology Information (NCBI).

FIG. 3 is a conversion table illustrating a correspondence between nucleic acid base triplets and amino acids.

FIG. 4 is a graph illustrating a rapid increase in the concentration of Replikin patterns in a selected strain of Hemagglutinin prior to the outbreak of three "Bird Flu" epidemics.

FIG. 5 is a table illustrating selected examples of Replikin patterns that have been found in various organisms.

FIG. 8 is a flow chart illustrating a generalized method for locating a plurality of Replikin-like patterns in a sequence of amino acids, according to an embodiment of the present invention.

FIG. 9 is a source code listing containing a procedure for discovering Replikin patterns in a sequence of amino acids, in accordance with an embodiment of the present invention.

FIG. 10. is a table illustrating Replikin scaffolds occurring in substantially fixed amino acid positions in different proteins.

DETAILED DESCRIPTION

Figure 6:
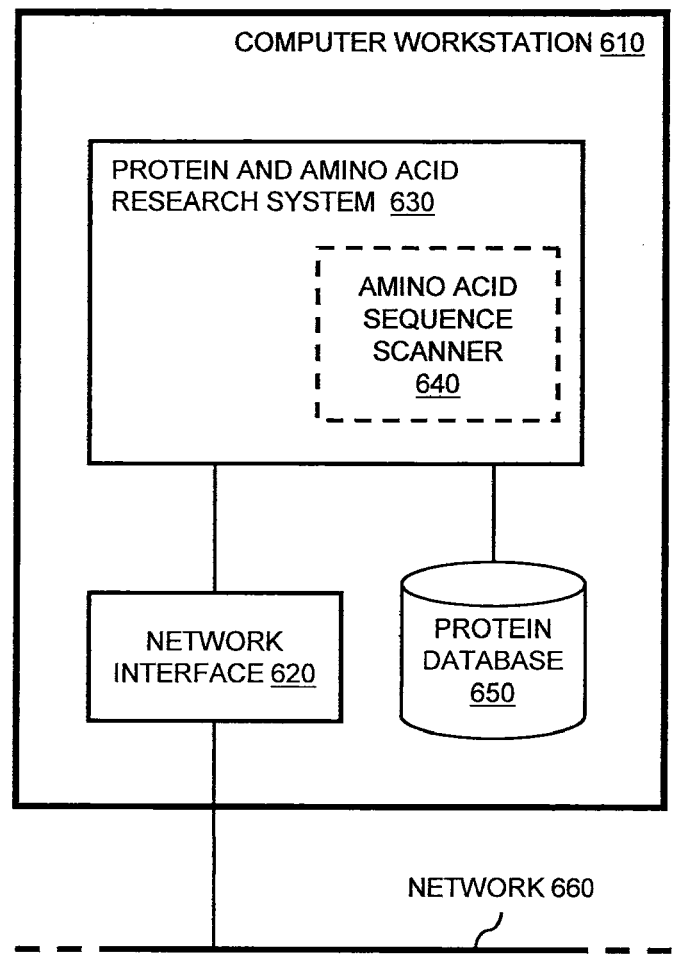
FIG. 6 is a high-level block diagram of a computer system incorporating a system and method for identifying Replikin patterns in amino acid sequences, in accordance with an embodiment of the present invention.

Embodiments of the present invention are directed to a system and method for identifying and/or locating complex patterns in an amino acid sequence. According to an aspect of the present invention, techniques are provided to facilitate queries of protein databases. For protein descriptions received in response to the queries, embodiments of the present invention may scan the received protein descriptions to identify and locate Replikin patterns. According to an embodiment, a Replikin pattern is a sequence of from 7 to about 50 amino acids that include the following three (3) characteristics, each of which may be recognized by an embodiment of the present invention: (1) the sequence has at least one lysine residue located six to ten amino acid residues from a second lysine residue; (2) the sequence has at least one histidine residue; and (3) at least 6% of the amino acids in the sequence are lysine residues. Another embodiment of the present invention may identify and/or locate a complex amino acid sequence having specified length constraints, which further includes any combination of the following characteristics: (1) a first amino acid residue located more than N positions and less than M positions away from a second amino acid residue; (2) a third amino acid residue located anywhere in the sequence; and (3) at least R percent of a fourth amino acid residue. According to yet another embodiment, the present invention may count occurrences of the identified amino acid sequences and may report the counted occurrences, either as raw absolute values or as ratios of the number of identified amino acid sequences per N amino acids in the protein. Still another embodiment of the present invention may analyze the evolution of identified amino acid sequence patterns in variants of a given protein over time, and may also analyze the similarities and differences between instances of identified amino acid sequence patterns across a plurality of different proteins over time. As a result of the analysis, yet another embodiment of the present invention may identify potential amino acid scaffolding structures that appear to be preserved over time and across different proteins, as component elements of the identified amino acid sequence patterns mutate and/or evolve.

Embodiments of the present invention will be described with reference to the accompanying drawings, wherein like parts are designated by like reference numerals throughout, and wherein the leftmost digit of each reference number refers to the drawing number of the figure in which the referenced part first appears.

FIG. 6 is a high-level block diagram of a computer system incorporating a system and method for identifying Replikin patterns in amino acid sequences, in accordance with an embodiment of the present invention. As shown in FIG. 6, computer workstation 610 may be a computer having a processor and a memory configured to permit a researcher to search protein databases and to scan protein descriptions for selected amino acid patterns. To accomplish these functions, computer workstation 610 may include protein and amino acid research system 630, which may receive instructions from a user/researcher to conduct protein searching and amino acid scanning operations. According to an embodiment, protein and amino acid research system 630 may further include amino acid sequence scanner 640 that scans and searches retrieved protein and amino acid sequences for specific patterns of amino acids, including Replikin patterns. Protein and amino acid research system 630 may communicate with network interface 620 to obtain protein sequences and amino acid sequences from resources on network 660, which may include the Internet. Alternatively, protein and amino acid research system 630 may obtain protein sequences and amino acid sequences from a local protein database 650. In addition, protein and amino acid research system 630 may obtain protein sequences and amino acid sequences directly from other input means, such as keyboard input. Protein and amino acid research system 630 may also communicate with network interface 620 to transmit results to other computers on network 660.

Scanning for Replikin Patterns

Figure 7:
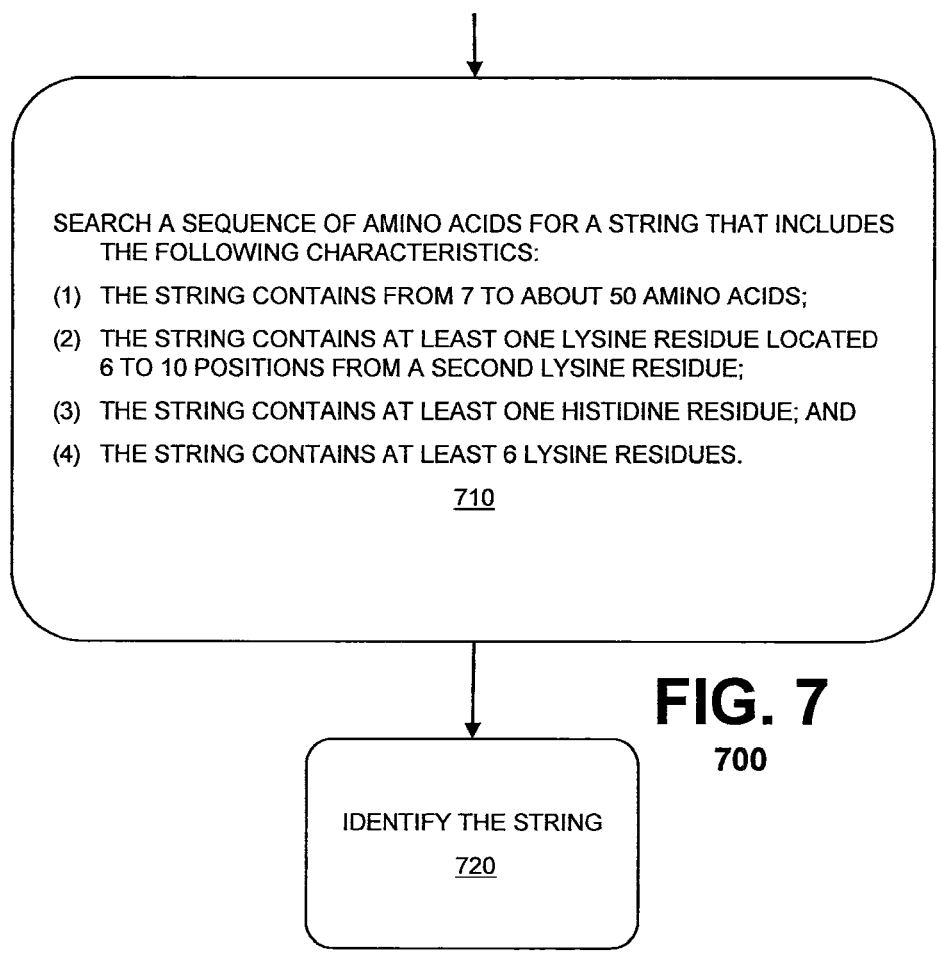
FIG. 7 is a simple flow chart illustrating a general method for locating a Replikin pattern in a sequence of amino acids, according to an embodiment of the present invention.

Embodiments of the present invention may include a generalized method and system for identifying complex patterns of amino acids within proteins. For any protein definition identified or selected by protein and amino acid research system 630, the user may direct embodiments of the invention to search for a variety of complex patterns of amino acids. As an example of one pattern of amino acids, the present invention provides a method for identifying nucleotide or amino acid sequences that include a Replikin pattern. FIG. 7 is a simple flow chart illustrating a general method for locating a Replikin pattern in a sequence of amino acids, according to an embodiment of the present invention. The method 700 may begin after a sequence of amino acids has been obtained. Typically, the sequence of amino acids may be represented by alphabetic characters according to the code supplied in FIG. 1. However, other encodings are envisioned by the present invention as well.

Referring to FIG. 7, once a sequence of amino acids has been obtained, the sequence is searched for a Replikin pattern (710), which comprises a subsequence (or string) of amino acids that includes the following characteristics:

(1) the string contains from 7 to about 50 amino acids;
(2) the string contains at least one lysine residue located 6 to 10 positions from a second lysine residue;
(3) the string contains at least one histidine residue; and
(4) the string contains at least 6% lysine residues.

Once a string of amino acids is found to match the Replikin pattern, the string may be identified or marked (720) accordingly.

A given sequence of amino acids may contain many subsequences or strings that match the Replikin pattern. Additionally, Replikin patterns may overlap each other. Thus, to locate and identify all possible Replikin patterns in a sequence of amino acids, method 700 may be invoked iteratively for each subsequence of amino acids contained within the original sequence of amino acids.

When method 700 is invoked iteratively to identify and locate all possible Replikin patterns in an amino acid sequence, an embodiment of the present invention may count the number of resulting Replikin patterns. A Replikin count may be reported as an absolute number. Additionally, embodiments of the invention may also determine a ratio of the number of Replikins per N amino acids in the sequence. For example, an embodiment may determine that a given protein contains a ratio of 6 Replikins for every 100 amino acids. Replikin ratios have been shown by laboratory experiment and by epidemiological evidence to correlate directly to the rate that a given protein replicates. Rapid replication of proteins may be an indication of disease. For example, the presence of relatively high ratios of Replikin patterns has been correlated to epidemics of influenza. Similarly, an increase in the count of Replikin patterns observed in a protein over time may also be an indication of future disease caused by the organism from which the protein was obtained (see, e.g., FIG. 4). Thus, the ability to detect and count Replikin patterns within sequences of amino acids is a significant advantage of the present invention.

Still referring to FIG. 7, embodiments of the present invention may utilize method 700 to identify and locate other complex patterns of amino acids, which exhibit characteristics similar to Replikin patterns. That is, although some embodiments of the present invention may specify exact values for: (1) distances between amino acids, (2) acceptable lengths of recognized amino acid sequences, and (3) the percentage or concentration of specific amino acids, these exact values may also be expressed as variables. Thus a researcher may employ an embodiment of the present invention to identify sequences of amino acids in a protein that have the following characteristics:

(1) the sequence contains from rmin to rmax amino acids;
(2) the sequence contains at least one lysine residue located kmin to kmax amino acid residues from a second lysine residue;
(3) the sequence contains at least one histidine residue; and
(4) the sequence contains at least kpercent lysine residues.

FIG. 8 is a flow chart illustrating a generalized method 800 for locating a plurality of Replikin-like patterns in a given sequence of amino acids, according to an embodiment of the present invention. The method 800 begins by locating a first lysine residue in the given sequence (810). Then, the method 800 may determine whether a second lysine residue resides within kmin to kmax positions of the first lysine residue (820). As indicated in FIG. 8, kmin and kmax define the limits on the distance between the first and second lysine residues. For a typical Replikin pattern, kmin will equal 6 and kmax will equal 10. However, these values may be varied by a researcher interested in discovering other similar patterns.

Once method 800 has identified two lysine residues that are close enough to each other (820), the method 800 may examine every histidine residue that resides within rmax positions of both the first and second lysine residues (830). When method 800 is employed to identify and locate typical Replikin patterns, rmax will usually be set to equal 50. For every histidine residue that resides within rmax positions of the two lysine residues identified in steps (810) and (820), method 800 will construct the shortest string of amino acid residues that includes the first lysine residue, the second lysine residue, and the identified histidine residue (840). Then, method 800 will determine whether the length of that shortest string is within the desired range—that is, whether it contains at least rmin amino acid residues and no more than rmax amino acid residues (850). Finally, if the identified string of amino acids also contains at least kpercent of lysine residues (860), the string will be identified as matching the desired Replikin-like pattern (870).

Still referring to FIG. 8, it is apparent that method 800 may identify several Replikin-like patterns from a single given amino acid sequence. This may happen because method 800 may examine more than one histidine residue that resides within rmax positions of the two identified lysine residues. Each identified histidine residue may, in combination with the two lysine residues, match the desired Replikin-like pattern.

One embodiment of the method illustrated by FIG. 8 is shown in FIG. 9, which is a source code listing containing a procedure for discovering all Replikin patterns present in a given sequence of amino acids, in accordance with an embodiment of the present invention. The "match" procedure shown in FIG. 9 is programmed in an interpreted shell language called "Tcl" and recognizes Replikins in a straightforward fashion. As known in the art, the "Tool Command Language" or Tcl (pronounced "tickle") is a simple interpreted scripting language that has its roots in the Unix command shells, but which has additional capabilities that are well-suited to network communication, Internet functionality and the rapid development of graphical user interfaces.

Alternative methods of recognizing Replikin patterns are also covered by the teachings of the present invention. For example, the match procedure shown in FIG. 9 could be implemented in other programming languages such as Java or C or C++. Additionally, alternative embodiments of the Replikin recognizing algorithm may identify the characteristics of a Replikin pattern in any order, and may also traverse component amino acid sequences and subsequences using recursive techniques, iterative techniques, parallel processing techniques, divide-and-conquer techniques or any combination thereof.

Protein Search Engine

Returning to FIG. 6, the present invention may include a search engine to access and interact with amino acid and protein databases, either locally or over a network such as the Internet, to retrieve protein definitions. For example, protein and amino acid research system 630 may accept protein search criteria from a user, and may then access a plurality of on-line amino acid and protein database search engines to retrieve protein definitions that match the supplied search criteria. Protein database search criteria may comprise any text string that may form a valid search term in any of the on-line protein or amino acid search engines. Typically, these search criteria relate to text that may be found in the printout that describes each specific protein. For example, if the user supplied the search criteria "influenza type A," embodiments of the present invention may forward this text string to a plurality of Internet protein and amino acid search engines, each of which may then return any protein descriptions found in their databases that contained the terms "influenza type A." Employing amino acid sequence scanner 640, each of the returned protein descriptions may be scanned for the presence of Replikin patterns.

Additional embodiments of the present invention may permit a user to select or de-select a plurality of Internet protein search engines and to customize the search criteria and protein retrieval capabilities of the present invention for each of the selected on-line protein search engines. Moreover, embodiments of the invention may also permit a user to access a local protein database 650 or to supply a specific protein definition directly, for example, by supplying a local file name containing the protein definition, or by other methods known in the art for supplying parameters to computer software.

Replikin Analysis

Embodiments of the present invention may be employed not only to identify and locate Replikin patterns in amino acid sequences. Embodiments may also be used to discover and analyze similarities in the structure of Replikin patterns occurring in different proteins, or to analyze different Replikin patterns occurring in the same protein over time. FIG. 10, for example, is a table illustrating a Replikin "fixed scaffold" structure that was preserved in a "Bird Flu" influenza virus over an 87 year period from 1917 to 2004. Embodiments of the present invention may assemble a number of discovered Replikin patterns in proteins, including Replikin patterns discovered in variants of the same protein. Along with each Replikin pattern, embodiments of the present invention may also associate a date when each protein was first identified. When directed by a researcher, an embodiment may sort and display a plurality of selected Replikin patterns according to content, date or other criteria, in order to reveal substantially fixed amino acid structures that have been preserved in Replikin patterns over time and which may be present in different proteins as well as variants of the same protein. Further, when directed by a researcher, an embodiment may employ, known methods of pattern analysis to compare a plurality of selected Replikin patterns in order to identify such fixed amino acid structures automatically. As an example, in FIG. 10, the illustrated Replikin patterns appear to demonstrate—in this case—a relatively fixed scaffold structure of (usually) 29 amino acids that begins with a pair of lysine residues (kk) at the amino terminal, ends with a pair of histidine residues (hh) at the carboxyl terminal, and contains a lysine residue in either position 8, 10 or 11. This conservation of scaffold structure over decades permits synthetic vaccines to be prepared rapidly and inexpensively. To synthesize such vaccines after a Replikin scaffolding structure has been identified, a researcher may select elements of that scaffolding structure that are conserved over time and which are also present in a current variant of a protein. A vaccine may then be prepared based on the selected elements from the scaffolding structure. Because such vaccines are based on conserved scaffolding structures, they may be effective for multiple years and may also be developed well in advance of an anticipated outbreak.

The discovery of Replikins themselves, as well as embodiments of the present invention for identifying and locating Replikin patterns, provides targets for the identification of pathogens, as well as facilitates the development of anti-pathogen therapies, including vaccines. In general, knowledge of and identification of the Replikin family of peptides enables development of effective therapies and vaccines for any organism that harbors Replikins. Specifically, identification of Replikins provides for the detection of viruses and virus vaccine development, including the influenza virus. Further, identification of Replikins also provides for the detection of other pathogens, such as malaria, anthrax and small pox virus, in addition to enabling the development of therapies and vaccines that target Replikin structures. Additional examples provided by the identification of Replikins include the detection of infectious disease Replikins, cancer immune Replikins and structural protein Replikins.

Embodiments of the present invention enable important Replikin patterns of amino acids to be recognized, located and analyzed in manners that are not found in the prior art. Using prior art capabilities, researchers have been limited in by existing techniques for describing sequences of amino acids. Indeed, limitations of the prior art have in some ways dampened research in this field, since heretofore it has not been possible to specify sequences of amino acids that comprise non-linear attributes. Until the development of the methods and embodiments of the present invention, descriptions of amino acid sequences were limited to linear sequences containing, at most, repetitive substrings and logical constraints on substring content. Embodiments of the present invention enable a new class of amino acid sequences to be discovered, located and analyzed using tools not found in the prior art. This new class of amino acids is characterized by attributes such as specific amino acid concentration and distance relationships between specific amino acids. These attributes transcend simple contiguous ordering and thus are not easily described, discovered or located by existing methods known in the art.

Figure 11:
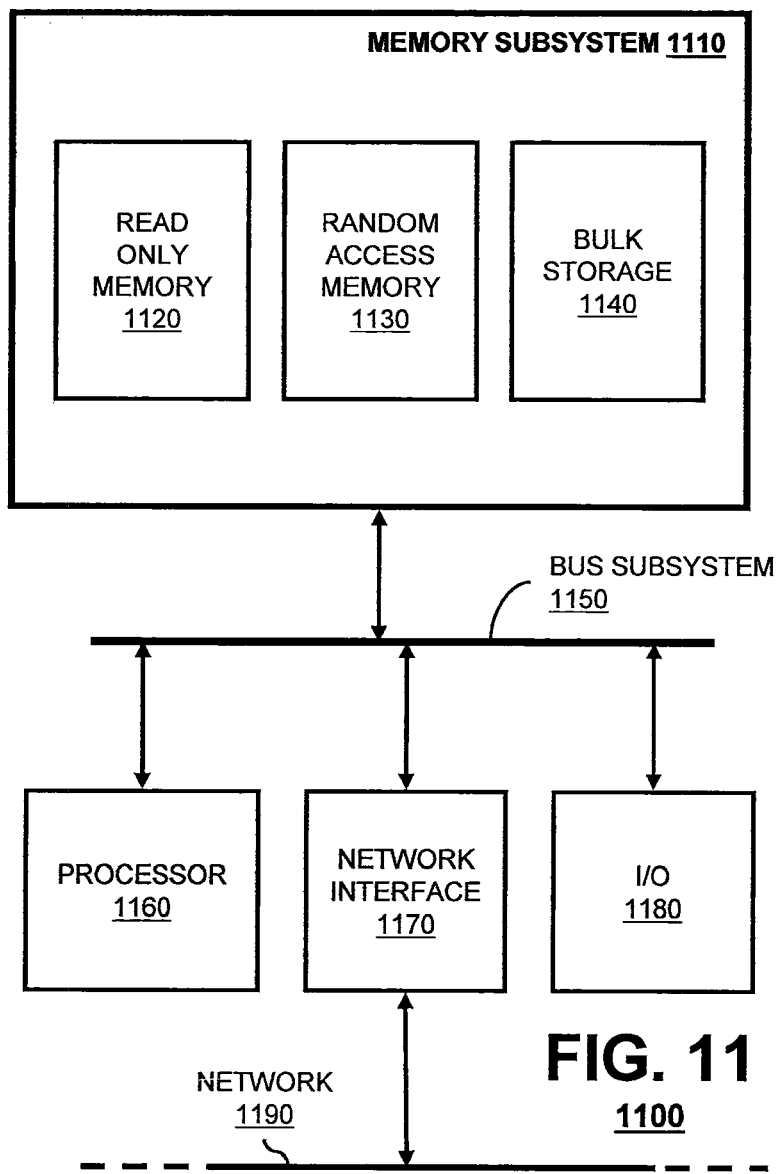
FIG. 11 is a simplified block diagram of a computer system platform useful with the present invention.

The functionality of the foregoing embodiments may be provided on various computer platforms executing program instructions. One such platform 1100 is illustrated in the simplified block diagram of FIG. 11. There, the platform 1100 is shown as being populated by a processor 1160, which communicates with a number of peripheral devices via a bus subsystem 1150. These peripheral devices typically include a memory subsystem 1110, a network interface subsystem 1170, and an input/output (I/O) unit 1180. The processor 1160 may be any of a plurality of conventional processing systems, including microprocessors, digital signal processors and field programmable logic arrays. In some applications, it may be advantageous to provide multiple processors (not shown) in the platform 1100. The processor(s) 1160 execute program instructions stored in the memory subsystem 1110. The memory subsystem 1110 may include any combination of conventional memory circuits, including electrical, magnetic or optical memory systems. As shown in FIG. 11, the memory system may include read only memories 1120, random access memories 1130 and bulk storage 1140. Memory subsystem 1110 not only stores program instructions representing the various methods described herein but also may store the data items on which these methods operate. Network interface subsystem 1170 may provide an interface to outside networks, including an interface to communications network 1190 comprising, for example, the Internet. I/O unit 1180 would permit communication with external devices, which are not shown.

Several embodiments of the present invention are specifically illustrated and described herein. However, it will be appreciated that modifications and variations of the present invention are covered by the teachings of the present invention without departing from the spirit and intended scope of the invention. Additionally, the teachings of the present invention may be adaptable to other sequence-recognizing problems that have heretofore been addressed using sequential linear analyses limited to the identification of specific sequences of component elements.

What is claimed is:

1. A method of determining a relative concentration of Replikin sequences in a protein or peptide of a pathogen, comprising:
  isolating at least one protein or peptide, counting the number of Replikin sequences in a sequence of amino acid residues of said isolated protein or peptide wherein said Replikin sequences are recognized according to the method comprising identifying within said sequence of amino acid residues of said protein or peptide a subsequence of 7 to 50 amino acid residues comprising:
  (1) a lysine residue six to ten residues from another lysine residue;
  (2) a histidine residue; and
  (3) at least 6% lysine residues,
wherein said subsequence of 7 to 50 amino acid residues is the shortest subsequence of 7 to 50 amino acid residues that comprises said lysine residue six to ten residues from said another lysine residue and said histidine residue, recognizing said subsequence as a Replikin sequence, and determining a relative concentration of Replikin sequences in said protein or peptide, wherein said concentration is the number of Replikin sequences in said sequence of amino acid residues or any representation of the number of Replikin sequences in said sequence of amino acid residues.

2. The method of claim 1 wherein said representation of said number of Replikin sequences is the ratio of the counted number of Replikin sequences versus the total number of amino acid residues in said protein or peptide.

3. The method of claim 1, wherein the sequence of amino acid residues defining the protein or peptide is retrieved from a computer file.

4. The method of claim 1, wherein the sequence of amino acid residues defining the protein or peptide is retrieved from a database.

5. The method of claim 4, wherein the database is accessed through a network.

6. A method of forecasting onset of disease, comprising:

determining a first concentration of Replikin sequences occurring in a protein at a first time according to the method of claim 1;

determining a second concentration of Replikin sequences occurring in the protein at a second time according to the method of claim 1; and reporting an increased probability of future disease caused by an organism harboring the protein when the second concentration is greater than the first concentration.

7. A method of determining a relative concentration of Replikin sequences in a protein or peptide of a pathogen, comprising;

counting the number of Replikin sequences in a sequence of amino acid residues of a protein or peptide wherein said Replikin sequences are recognized according to the method comprising identifying within said sequence of amino acid residues of said protein or peptide a subsequence of 7 to 50 amino acid residues comprising:

(1) a lysine residue six to ten residues from another lysine residue;

(2) a histidine residue; and (3) at least 6% lysine residues, wherein said subsequence of 7 to 50 amino acid residues is the shortest subsequence of 7 to 50 amino acid residues that comprises said lysine residue six to ten residues from said another lysine residue and said histidine residue, recognizing said subsequence as a Replikin sequence, determining a relative concentration of Replikin sequences in said protein or peptide, wherein said concentration is the number of Replikin sequences in said sequence of amino acid residues or any representation of the number of Replikin sequences in said sequence of amino acid residues, wherein at least one step of said method of determining a concentration of Replikin sequences in a protein or peptide is practiced on a processor.

8. The method of claim 7, wherein the sequence of amino acid residues defining the protein or peptide is retrieved from a computer file.

9. The method of claim 7, wherein the sequence of amino acid residues defining the protein or peptide is retrieved from a database.

10. The method of claim 9, wherein the database is accessed through a network.

11. A method of forecasting onset of disease, comprising:

determining a first concentration of Replikin sequences occurring in a protein at a first time according to the method of claim 7;

determining a second concentration of Replikin sequences occurring in the protein at a second time according to the method of claim 7; and reporting an increased probability of future disease caused by an organism harboring the protein when the second concentration is greater than the first concentration.

* * * * *

SEQUENCE LISTING

```
<160> NUMBER OF SEQ ID NOS: 108

<210> SEQ ID NO 1
<211> LENGTH: 10
<212> TYPE: PRT
<213> ORGANISM: Homo sapiens

<400> SEQUENCE: 1

Met Tyr Arg Pro Asp Val Val Arg Ala Arg
  1               5                  10

<210> SEQ ID NO 2
<211> LENGTH: 29
<212> TYPE: PRT
<213> ORGANISM: Influenza virus
<220> FEATURE:
<221> NAME/KEY: MOD_RES
<222> LOCATION: (13)
<223> OTHER INFORMATION: Variable amino acid

<400> SEQUENCE: 2

Lys Lys Asn Ser Ala Tyr Pro Thr Ile Lys Arg Ser Xaa Asn Asn Thr
  1               5                  10                  15

Asn His Glu Asp Leu Leu Val Leu Trp Gly Ile His His
             20                  25

<210> SEQ ID NO 3
<211> LENGTH: 379
<212> TYPE: PRT
<213> ORGANISM: Unknown Organism
<220> FEATURE:
<223> OTHER INFORMATION: Description of Unknown Organism: Uknown TVFV2E
      envelope protein
<220> FEATURE:
<221> NAME/KEY: MOD_RES
<222> LOCATION: (322)..(343)
<223> OTHER INFORMATION: Variable amino acid

<400> SEQUENCE: 3

Glu Leu Arg Leu Arg Tyr Cys Ala Pro Ala Gly Phe Ala Leu Leu Lys
  1               5                  10                  15

Cys Asn Asp Ala Asp Tyr Asp Gly Phe Lys Thr Asn Cys Ser Asn Val
             20                  25                  30

```
Ser Val Val His Cys Thr Asn Leu Met Asn Thr Thr Val Thr Thr Gly
            35                  40                  45

Leu Leu Leu Asn Gly Ser Tyr Ser Glu Asn Arg Thr Gln Ile Trp Gln
 50                  55                  60

Lys His Arg Thr Ser Asn Asp Ser Ala Leu Ile Leu Leu Asn Lys His
 65                  70                  75                  80

Tyr Asn Leu Thr Val Thr Cys Lys Arg Pro Gly Asn Lys Thr Val Leu
                 85                  90                  95

Pro Val Thr Ile Met Ala Gly Leu Val Phe His Ser Gln Lys Tyr Asn
                100                 105                 110

Leu Arg Leu Arg Gln Ala Trp Cys His Phe Pro Ser Asn Trp Lys Gly
            115                 120                 125

Ala Trp Lys Glu Val Lys Glu Glu Ile Val Asn Leu Pro Lys Glu Arg
130                 135                 140

Tyr Arg Gly Thr Asn Asp Pro Lys Arg Ile Phe Phe Gln Arg Gln Trp
145                 150                 155                 160

Gly Asp Pro Glu Thr Ala Asn Leu Trp Phe Asn Cys His Gly Glu Phe
                165                 170                 175

Phe Tyr Cys Lys Met Asp Trp Phe Leu Asn Tyr Leu Asn Asn Leu Thr
            180                 185                 190

Val Asp Ala Asp His Asn Glu Cys Lys Asn Thr Ser Gly Thr Lys Ser
            195                 200                 205

Gly Asn Lys Arg Ala Pro Gly Pro Cys Val Gln Arg Thr Tyr Val Ala
210                 215                 220

Cys His Ile Arg Ser Val Ile Ile Trp Leu Glu Thr Ile Ser Lys Lys
225                 230                 235                 240

Thr Tyr Ala Pro Pro Arg Glu Gly His Leu Glu Cys Thr Ser Thr Val
                245                 250                 255

Thr Gly Met Thr Val Glu Leu Asn Tyr Ile Pro Lys Asn Arg Thr Asn
            260                 265                 270

Val Thr Leu Ser Pro Gln Ile Glu Ser Ile Trp Ala Ala Glu Leu Asp
            275                 280                 285

Arg Tyr Lys Leu Val Glu Ile Thr Pro Ile Gly Phe Ala Pro Thr Glu
290                 295                 300

Val Arg Arg Tyr Thr Gly Gly His Glu Arg Gln Lys Arg Val Pro Phe
305                 310                 315                 320

Val Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Val Gln Ser Gln His Leu Leu Ala Gly
            340                 345                 350

Ile Leu Gln Gln Gln Lys Asn Leu Leu Ala Ala Val Glu Ala Gln Gln
            355                 360                 365

Gln Met Leu Lys Leu Thr Ile Trp Gly Val Lys
            370                 375

<210> SEQ ID NO 4
<211> LENGTH: 422
<212> TYPE: PRT
<213> ORGANISM: Homo sapiens

<400> SEQUENCE: 4

Met Tyr Arg Pro Asp Val Val Arg Ala Arg Lys Arg Val Cys Trp Glu
  1               5                  10                  15

Pro Trp Val Ile Gly Leu Val Ile Phe Ile Ser Leu Ile Val Leu Ala
                 20                  25                  30
```

```
Val Cys Ile Gly Leu Thr Val His Tyr Val Arg Tyr Asn Gln Lys Lys
             35                  40                  45

Thr Tyr Asn Tyr Tyr Ser Thr Leu Ser Phe Thr Thr Asp Lys Leu Tyr
     50                  55                  60

Ala Glu Phe Gly Arg Glu Ala Ser Asn Asn Phe Thr Glu Met Ser Gln
 65                  70                  75                  80

Arg Leu Glu Ser Met Val Lys Asn Ala Phe Tyr Lys Ser Pro Leu Arg
                 85                  90                  95

Glu Glu Phe Val Lys Ser Gln Val Ile Lys Phe Ser Gln Gln Lys His
            100                 105                 110

Gly Val Leu Ala His Met Leu Leu Ile Cys Arg Phe His Ser Thr Glu
            115                 120                 125

Asp Pro Glu Thr Val Asp Lys Ile Val Gln Leu Val Leu His Glu Lys
    130                 135                 140

Leu Gln Asp Ala Val Gly Pro Pro Lys Val Asp Pro His Ser Val Lys
145                 150                 155                 160

Ile Lys Lys Ile Asn Lys Thr Glu Thr Asp Ser Tyr Leu Asn His Cys
                    165                 170                 175

Cys Gly Thr Arg Arg Ser Lys Thr Leu Gly Gln Ser Leu Arg Ile Val
                180                 185                 190

Gly Gly Thr Glu Val Glu Glu Gly Trp Pro Trp Gln Ala Ser Leu
            195                 200                 205

Gln Trp Asp Gly Ser His Arg Cys Gly Ala Thr Leu Ile Asn Ala Thr
    210                 215                 220

Trp Leu Val Ser Ala Ala His Cys Phe Thr Thr Tyr Lys Asn Pro Ala
225                 230                 235                 240

Arg Trp Thr Ala Ser Phe Gly Val Thr Ile Lys Pro Ser Lys Met Lys
                    245                 250                 255

Arg Gly Leu Arg Arg Ile Ile Val His Glu Lys Tyr Lys His Pro Ser
                260                 265                 270

His Asp Tyr Asp Ile Ser Leu Ala Glu Leu Ser Ser Pro Val Pro Tyr
        275                 280                 285

Thr Asn Ala Val His Arg Val Cys Leu Pro Asp Ala Ser Tyr Glu Phe
    290                 295                 300

Gln Pro Gly Asp Val Met Phe Val Thr Gly Phe Gly Ala Leu Lys Asn
305                 310                 315                 320

Asp Gly Tyr Ser Gln Asn His Leu Arg Gln Ala Gln Val Thr Leu Ile
                    325                 330                 335

Asp Ala Thr Thr Cys Asn Glu Pro Gln Ala Tyr Asn Asp Ala Ile Thr
                340                 345                 350

Pro Arg Met Leu Cys Ala Gly Ser Leu Glu Gly Lys Thr Asp Ala Cys
        355                 360                 365

Gln Gly Asp Ser Gly Gly Pro Leu Val Ser Ser Asp Ala Arg Asp Ile
    370                 375                 380

Trp Tyr Leu Ala Gly Ile Val Ser Trp Gly Asp Glu Cys Ala Lys Pro
385                 390                 395                 400

Asn Lys Pro Gly Val Tyr Thr Arg Val Thr Ala Leu Arg Asp Trp Ile
                    405                 410                 415

Thr Ser Lys Thr Gly Ile
                420
```

<210> SEQ ID NO 5
<211> LENGTH: 29
<212> TYPE: PRT
<213> ORGANISM: Influenza virus -continued

```
<400> SEQUENCE: 5

Lys Lys Gly Thr Ser Tyr Pro Lys Leu Ser Lys Ser Tyr Thr Asn Asn
 1               5                  10                  15

Lys Gly Lys Glu Val Leu Val Leu Trp Gly Val His His
            20                  25

<210> SEQ ID NO 6
<211> LENGTH: 29
<212> TYPE: PRT
<213> ORGANISM: Influenza virus

<400> SEQUENCE: 6

Lys Lys Gly Ser Ser Tyr Pro Lys Leu Ser Lys Ser Tyr Val Asn Asn
 1               5                  10                  15

Lys Gly Lys Glu Val Leu Val Leu Trp Gly Val His His
            20                  25

<210> SEQ ID NO 7
<211> LENGTH: 29
<212> TYPE: PRT
<213> ORGANISM: Influenza virus

<400> SEQUENCE: 7

Lys Lys Glu Asn Ser Tyr Pro Lys Leu Ser Lys Ser Tyr Val Asn Asn
 1               5                  10                  15

Lys Gly Lys Glu Val Leu Val Leu Trp Gly Val His His
            20                  25

<210> SEQ ID NO 8
<211> LENGTH: 29
<212> TYPE: PRT
<213> ORGANISM: Influenza virus

<400> SEQUENCE: 8

Lys Lys Gly Asp Ser Tyr Pro Lys Leu Thr Asn Ser Tyr Val Asn Asn
 1               5                  10                  15

Lys Gly Lys Glu Val Leu Val Leu Trp Gly Val His His
            20                  25

<210> SEQ ID NO 9
<211> LENGTH: 29
<212> TYPE: PRT
<213> ORGANISM: Influenza virus

<400> SEQUENCE: 9

Lys Lys Gly Thr Ser Tyr Pro Lys Leu Ser Lys Ser Tyr Thr Asn Asn
 1               5                  10                  15

Lys Gly Lys Glu Val Leu Val Leu Trp Gly Val His His
            20                  25

<210> SEQ ID NO 10
<211> LENGTH: 9
<212> TYPE: PRT
<213> ORGANISM: Mycoplasma pulmonis

<400> SEQUENCE: 10

Lys Lys Glu Lys Thr Thr His Asn Lys
 1               5

<210> SEQ ID NO 11
<211> LENGTH: 29
<212> TYPE: PRT
<213> ORGANISM: Influenza virus
```

```
<400> SEQUENCE: 11

Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25

<210> SEQ ID NO 12
<211> LENGTH: 29
<212> TYPE: PRT
<213> ORGANISM: Influenza virus

<400> SEQUENCE: 12

Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25

<210> SEQ ID NO 13
<211> LENGTH: 29
<212> TYPE: PRT
<213> ORGANISM: Influenza virus

<400> SEQUENCE: 13

Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25

<210> SEQ ID NO 14
<211> LENGTH: 29
<212> TYPE: PRT
<213> ORGANISM: Influenza virus

<400> SEQUENCE: 14

Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25

<210> SEQ ID NO 15
<211> LENGTH: 29
<212> TYPE: PRT
<213> ORGANISM: Influenza virus

<400> SEQUENCE: 15

Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25

<210> SEQ ID NO 16
<211> LENGTH: 29
<212> TYPE: PRT
<213> ORGANISM: Influenza virus

<400> SEQUENCE: 16

Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25
```

```
<210> SEQ ID NO 17
<211> LENGTH: 29
<212> TYPE: PRT
<213> ORGANISM: Influenza virus

<400> SEQUENCE: 17

Lys Lys Gly Thr Ser Tyr Pro Lys Leu Ser Lys Ser Tyr Thr Asn Asn
 1               5                  10                  15

Lys Gly Lys Glu Val Leu Val Leu Trp Gly Val His His
            20                  25

<210> SEQ ID NO 18
<211> LENGTH: 13
<212> TYPE: PRT
<213> ORGANISM: Hepatitis C virus

<400> SEQUENCE: 18

His Tyr Pro Pro Lys Pro Gly Cys Ile Val Pro Ala Lys
 1               5                  10

<210> SEQ ID NO 19
<211> LENGTH: 29
<212> TYPE: PRT
<213> ORGANISM: Influenza virus

<400> SEQUENCE: 19

Lys Lys Gly Asn Ser Tyr Pro Lys Leu Ser Lys Ser Tyr Thr Asn Asn
 1               5                  10                  15

Lys Gly Lys Glu Val Leu Val Ile Trp Gly Val His His
            20                  25

<210> SEQ ID NO 20
<211> LENGTH: 29
<212> TYPE: PRT
<213> ORGANISM: Influenza virus

<400> SEQUENCE: 20

Lys Lys Gly Asn Ser Tyr Pro Lys Leu Ser Lys Ser Tyr Thr Asn Asn
 1               5                  10                  15

Lys Gly Lys Glu Val Leu Val Ile Trp Gly Val His His
            20                  25

<210> SEQ ID NO 21
<211> LENGTH: 29
<212> TYPE: PRT
<213> ORGANISM: Influenza virus

<400> SEQUENCE: 21

Lys Lys Gly Asn Ser Tyr Pro Lys Leu Ser Lys Ser Tyr Thr Asn Asn
 1               5                  10                  15

Lys Gly Lys Glu Val Leu Val Ile Trp Gly Val His His
            20                  25

<210> SEQ ID NO 22
<211> LENGTH: 29
<212> TYPE: PRT
<213> ORGANISM: Influenza virus

<400> SEQUENCE: 22

Lys Lys Gly Asp Ser Tyr Pro Lys Leu Ser Lys Ser Tyr Thr Asn Asn
 1               5                  10                  15

Lys Gly Lys Glu Val Leu Val Ile Trp Gly Val His His
            20                  25
```

<210> SEQ ID NO 23
<211> LENGTH: 29
<212> TYPE: PRT
<213> ORGANISM: Influenza virus

<400> SEQUENCE: 23

Lys Lys Gly Ser Ser Tyr Pro Lys Leu Ser Lys Ser Tyr Val Asn Asn
 1               5                  10                  15

Lys Gly Lys Glu Val Leu Val Leu Trp Gly Val His His
            20                  25

<210> SEQ ID NO 24
<211> LENGTH: 29
<212> TYPE: PRT
<213> ORGANISM: Influenza virus

<400> SEQUENCE: 24

Lys Lys Gly Ser Ser Tyr Pro Lys Leu Ser Lys Ser Tyr Val Asn Asn
 1               5                  10                  15

Lys Gly Lys Glu Val Leu Val Leu Trp Gly Val His His
            20                  25

<210> SEQ ID NO 25
<211> LENGTH: 29
<212> TYPE: PRT
<213> ORGANISM: Influenza virus

<400> SEQUENCE: 25

Lys Lys Gly Asn Ser Tyr Pro Lys Leu Ser Lys Ser Tyr Thr Asn Asn
 1               5                  10                  15

Lys Gly Lys Glu Val Leu Val Ile Trp Gly Val His His
            20                  25

<210> SEQ ID NO 26
<211> LENGTH: 29
<212> TYPE: PRT
<213> ORGANISM: Influenza virus

<400> SEQUENCE: 26

Lys Lys Gly Asn Ser Tyr Pro Lys Leu Ser Lys Ser Tyr Thr Asn Asn
 1               5                  10                  15

Lys Gly Lys Glu Val Leu Val Ile Trp Gly Val His His
            20                  25

<210> SEQ ID NO 27
<211> LENGTH: 29
<212> TYPE: PRT
<213> ORGANISM: Influenza virus

<400> SEQUENCE: 27

Lys Lys Gly Asn Ser Tyr Pro Lys Leu Ser Lys Ser Tyr Thr Asn Asn
 1               5                  10                  15

Lys Gly Lys Glu Val Leu Val Ile Trp Gly Val His His
            20                  25

<210> SEQ ID NO 28
<211> LENGTH: 29
<212> TYPE: PRT
<213> ORGANISM: Influenza virus

```
<400> SEQUENCE: 28

Lys Lys Gly Asn Ser Tyr Pro Lys Leu Ser Lys Ser Tyr Thr Asn Asn
 1               5                  10                  15

Lys Gly Lys Glu Val Leu Val Ile Trp Gly Val His His
            20                  25

<210> SEQ ID NO 29
<211> LENGTH: 29
<212> TYPE: PRT
<213> ORGANISM: Influenza virus

<400> SEQUENCE: 29

Lys Lys Gly Asn Ser Tyr Pro Lys Ile Ser Lys Ser Tyr Ile Asn Asn
 1               5                  10                  15

Lys Glu Lys Glu Val Leu Val Leu Trp Gly Ile His His
            20                  25

<210> SEQ ID NO 30
<211> LENGTH: 29
<212> TYPE: PRT
<213> ORGANISM: Influenza virus

<400> SEQUENCE: 30

Lys Lys Gly Asn Ser Tyr Pro Lys Leu Ser Lys Ser Tyr Ile Asn Asn
 1               5                  10                  15

Lys Lys Lys Glu Val Leu Val Ile Trp Gly Ile His His
            20                  25

<210> SEQ ID NO 31
<211> LENGTH: 29
<212> TYPE: PRT
<213> ORGANISM: Influenza virus

<400> SEQUENCE: 31

Lys Lys Gly Asn Ser Tyr Pro Lys Leu Ser Lys Ser Tyr Ile Asn Asn
 1               5                  10                  15

Lys Gly Lys Lys Val Leu Val Leu Trp Gly Ile His His
            20                  25

<210> SEQ ID NO 32
<211> LENGTH: 29
<212> TYPE: PRT
<213> ORGANISM: Influenza virus

<400> SEQUENCE: 32

Lys Lys Gly Thr Ser Tyr Pro Lys Leu Ser Lys Ser Tyr Thr Asn Asn
 1               5                  10                  15

Lys Lys Lys Glu Val Leu Val Leu Trp Gly Val His His
            20                  25

<210> SEQ ID NO 33
<211> LENGTH: 28
<212> TYPE: PRT
<213> ORGANISM: Influenza virus

<400> SEQUENCE: 33

Lys Asn Gly Leu Tyr Pro Asn Leu Ser Lys Ser Tyr Ala Asn Asn Lys
 1               5                  10                  15

Glu Lys Glu Val Leu Val Leu Trp Gly Val His His
            20                  25
```

<210> SEQ ID NO 34
<211> LENGTH: 28
<212> TYPE: PRT
<213> ORGANISM: Influenza virus

<400> SEQUENCE: 34

Lys Asn Gly Leu Tyr Pro Asn Leu Ser Lys Ser Tyr Ala Asn Asn Lys
 1               5                  10                  15
Glu Lys Glu Val Leu Ile Leu Trp Gly Val His His
            20                  25

<210> SEQ ID NO 35
<211> LENGTH: 29
<212> TYPE: PRT
<213> ORGANISM: Influenza virus

<400> SEQUENCE: 35

Lys Lys Glu Asn Ser Tyr Pro Lys Leu Arg Lys Ser Ile Ile Ile Asn
 1               5                  10                  15
Lys Lys Glu Val Lys Leu Val Ile Trp Gly Ile His His
            20                  25

<210> SEQ ID NO 36
<211> LENGTH: 19
<212> TYPE: PRT
<213> ORGANISM: Influenza virus

<400> SEQUENCE: 36

Lys Ser Tyr Lys Asn Thr Arg Lys Asp Pro Ala Leu Ile Ile Trp Gly
 1               5                  10                  15
Ile His His

<210> SEQ ID NO 37
<211> LENGTH: 29
<212> TYPE: PRT
<213> ORGANISM: Influenza virus

<400> SEQUENCE: 37

Lys Lys Gly Pro Asn Tyr Pro Val Ala Lys Arg Ser Tyr Asn Asn Thr
 1               5                  10                  15
Ser Gly Glu Gln Met Leu Ile Ile Trp Gly Val His His
            20                  25

<210> SEQ ID NO 38
<211> LENGTH: 29
<212> TYPE: PRT
<213> ORGANISM: Influenza virus

<400> SEQUENCE: 38

Lys Lys Gly Pro Asn Tyr Pro Val Ala Lys Arg Ser Tyr Asn Asn Thr
 1               5                  10                  15
Ser Gly Glu Gln Met Leu Ile Ile Trp Gly Ile His His
            20                  25

<210> SEQ ID NO 39
<211> LENGTH: 29
<212> TYPE: PRT
<213> ORGANISM: Influenza virus -continued

```
<400> SEQUENCE: 39

Lys Lys Asn Asn Ala Tyr Pro Thr Ile Lys Arg Thr Tyr Asn Asn Thr
1               5                   10                  15

Asn Val Glu Asp Leu Leu Ile Leu Trp Gly Ile His His
            20                  25

<210> SEQ ID NO 40
<211> LENGTH: 29
<212> TYPE: PRT
<213> ORGANISM: Influenza virus

<400> SEQUENCE: 40

Lys Lys Asn Asn Ala Tyr Pro Thr Ile Lys Arg Ser Tyr Ser Asn Thr
1               5                   10                  15

Asn Gln Glu Asp Leu Leu Val Leu Trp Gly Ile His His
            20                  25

<210> SEQ ID NO 41
<211> LENGTH: 29
<212> TYPE: PRT
<213> ORGANISM: Influenza virus

<400> SEQUENCE: 41

Lys Lys Asn Asn Ala Tyr Pro Thr Ile Lys Arg Thr Tyr Asn Asn Thr
1               5                   10                  15

Asn Ile Glu Asp Leu Leu Ile Leu Trp Gly Ile His His
            20                  25

<210> SEQ ID NO 42
<211> LENGTH: 29
<212> TYPE: PRT
<213> ORGANISM: Influenza virus

<400> SEQUENCE: 42

Lys Lys Asn Asn Ala Tyr Pro Thr Ile Lys Arg Thr Tyr Asn Asn Thr
1               5                   10                  15

Asn Met Glu Asp Leu Leu Ile Leu Trp Gly Ile His His
            20                  25

<210> SEQ ID NO 43
<211> LENGTH: 9
<212> TYPE: PRT
<213> ORGANISM: Unknown Organism
<220> FEATURE:
<223> OTHER INFORMATION: Description of Unknown Organism: Unknown
      macrophage infectivity potentiator peptide

<400> SEQUENCE: 43

Lys Val His Phe Phe Gln Leu Lys Lys
1               5

<210> SEQ ID NO 44
<211> LENGTH: 29
<212> TYPE: PRT
<213> ORGANISM: Influenza virus

<400> SEQUENCE: 44

Lys Lys Gly Asn Ala Tyr Pro Thr Ile Lys Arg Thr Tyr Asn Asn Thr
1               5                   10                  15

Asn Val Glu Asp Leu Leu Ile Leu Trp Gly Ile His His
            20                  25
```

```
<210> SEQ ID NO 45
<211> LENGTH: 29
<212> TYPE: PRT
<213> ORGANISM: Influenza virus

<400> SEQUENCE: 45

Lys Lys Asn Asn Thr Tyr Pro Thr Ile Lys Arg Ser Tyr Asn Asn Thr
 1               5                  10                  15

Asn Gln Glu Asp Leu Leu Ile Leu Trp Gly Ile His His
            20                  25

<210> SEQ ID NO 46
<211> LENGTH: 29
<212> TYPE: PRT
<213> ORGANISM: Influenza virus

<400> SEQUENCE: 46

Lys Lys Asn Ser Ala Tyr Pro Thr Ile Lys Arg Ser Tyr Asn Asn Thr
 1               5                  10                  15

Asn Gln Glu Asp Leu Leu Val Leu Trp Gly Ile His His
            20                  25

<210> SEQ ID NO 47
<211> LENGTH: 29
<212> TYPE: PRT
<213> ORGANISM: Influenza virus

<400> SEQUENCE: 47

Lys Lys Asn Ser Ala Tyr Pro Thr Ile Lys Arg Ser Tyr Asn Asn Thr
 1               5                  10                  15

Asn Gln Glu Asp Leu Leu Val Leu Trp Gly Ile His His
            20                  25

<210> SEQ ID NO 48
<211> LENGTH: 7
<212> TYPE: PRT
<213> ORGANISM: Rous sarcoma virus

<400> SEQUENCE: 48

Lys Lys Leu Arg His Glu Lys
 1               5

<210> SEQ ID NO 49
<211> LENGTH: 7
<212> TYPE: PRT
<213> ORGANISM: Avian sarcoma virus

<400> SEQUENCE: 49

Lys Lys Leu Arg His Asp Lys
 1               5

<210> SEQ ID NO 50
<211> LENGTH: 7
<212> TYPE: PRT
<213> ORGANISM: Unknown Organism
<220> FEATURE:
<223> OTHER INFORMATION: Description of Unknown Organism: Unknown
      c-yes, colon cancer peptide

<400> SEQUENCE: 50

Lys Lys Leu Arg His Asp Lys
 1               5
```

```
<210> SEQ ID NO 51
<211> LENGTH: 7
<212> TYPE: PRT
<213> ORGANISM: Avian sarcoma virus

<400> SEQUENCE: 51

Lys Lys Leu Arg His Glu Lys
 1               5

<210> SEQ ID NO 52
<211> LENGTH: 7
<212> TYPE: PRT
<213> ORGANISM: Homo sapiens

<400> SEQUENCE: 52

Lys Lys Leu Arg His Glu Lys
 1               5

<210> SEQ ID NO 53
<211> LENGTH: 8
<212> TYPE: PRT
<213> ORGANISM: Unknown Organism
<220> FEATURE:
<223> OTHER INFORMATION: Description of Unknown Organism: Unknown
      neuroblastoma oncogene peptide

<400> SEQUENCE: 53

Lys Gln Ala His Glu Leu Ala Lys
 1               5

<210> SEQ ID NO 54
<211> LENGTH: 8
<212> TYPE: PRT
<213> ORGANISM: Polyamavirus sp.

<400> SEQUENCE: 54

Lys Thr His Arg Phe Ser Lys His
 1               5

<210> SEQ ID NO 55
<211> LENGTH: 8
<212> TYPE: PRT
<213> ORGANISM: Sindbis virus

<400> SEQUENCE: 55

Lys Asn Leu His Glu Lys Ile Lys
 1               5

<210> SEQ ID NO 56
<211> LENGTH: 9
<212> TYPE: PRT
<213> ORGANISM: Human papilloamavirus type 71

<400> SEQUENCE: 56

Lys His Arg Pro Leu Leu Gln Leu Lys
 1               5

<210> SEQ ID NO 57
<211> LENGTH: 7
<212> TYPE: PRT
<213> ORGANISM: Unknown Organism
<220> FEATURE:
<223> OTHER INFORMATION: Description of Unknown Organism: Unknown
      v-erbB tumor virus peptide
```

```
<400> SEQUENCE: 57

Lys Ser Pro Asn His Val Lys
 1               5

<210> SEQ ID NO 58
<211> LENGTH: 8
<212> TYPE: PRT
<213> ORGANISM: Feline sarcoma virus

<400> SEQUENCE: 58

Lys Asn Ile His Leu Glu Lys Lys
 1               5

<210> SEQ ID NO 59
<211> LENGTH: 8
<212> TYPE: PRT
<213> ORGANISM: Unknown Organism
<220> FEATURE:
<223> OTHER INFORMATION: Description of Unknown Organism: Unknown
      c-fms myelomonocytic tumor peptide

<400> SEQUENCE: 59

Lys Asn Ile His Leu Glu Lys Lys
 1               5

<210> SEQ ID NO 60
<211> LENGTH: 10
<212> TYPE: PRT
<213> ORGANISM: Polyamavirus sp.

<400> SEQUENCE: 60

Lys Pro His Leu Ala Gln Ser Leu Glu Lys
 1               5                   10

<210> SEQ ID NO 61
<211> LENGTH: 9
<212> TYPE: PRT
<213> ORGANISM: Polyamavirus sp.

<400> SEQUENCE: 61

Lys Gln His Arg Glu Leu Lys Asp Lys
 1               5

<210> SEQ ID NO 62
<211> LENGTH: 9
<212> TYPE: PRT
<213> ORGANISM: Polyamavirus sp.

<400> SEQUENCE: 62

Lys Gln His Arg Glu Leu Lys Asp Lys
 1               5

<210> SEQ ID NO 63
<211> LENGTH: 12
<212> TYPE: PRT
<213> ORGANISM: Murine leukemia virus

<400> SEQUENCE: 63

Lys Val Pro Val Leu Ile Ser Pro Thr Leu Lys His
 1               5                   10

<210> SEQ ID NO 64
<211> LENGTH: 13
<212> TYPE: PRT
<213> ORGANISM: Human T-cell lymphotropic virus
```

```
<400> SEQUENCE: 64

Lys Ser Leu Leu Leu Glu Val Asp Lys Asp Ile Ser His
 1               5                  10

<210> SEQ ID NO 65
<211> LENGTH: 13
<212> TYPE: PRT
<213> ORGANISM: Unknown Organism
<220> FEATURE:
<223> OTHER INFORMATION: Description of Unknown Organism: Unknown
      c-kit, GI tumor peptide

<400> SEQUENCE: 65

Lys Ala Gly Ile Thr Ile Met Val Lys Arg Glu Tyr His
 1               5                  10

<210> SEQ ID NO 66
<211> LENGTH: 8
<212> TYPE: PRT
<213> ORGANISM: Unknown Organism
<220> FEATURE:
<223> OTHER INFORMATION: Description of Unknown Organism: Unknown
      transforming protein myb

<400> SEQUENCE: 66

Lys Ser Gly Lys His Leu Gly Lys
 1               5

<210> SEQ ID NO 67
<211> LENGTH: 9
<212> TYPE: PRT
<213> ORGANISM: Unknown Organism
<220> FEATURE:
<223> OTHER INFORMATION: Description of Unknown Organism: Unknown
      transforming protein myc

<400> SEQUENCE: 67

Lys Arg Arg Glu Gln Leu Lys His Lys
 1               5

<210> SEQ ID NO 68
<211> LENGTH: 10
<212> TYPE: PRT
<213> ORGANISM: Unknown Organism
<220> FEATURE:
<223> OTHER INFORMATION: Description of Unknown Organism: Unknown
      Ras-related GTP-binding protein

<400> SEQUENCE: 68

Lys Ser Phe Glu Val Ile Lys Val Ile His
 1               5                  10

<210> SEQ ID NO 69
<211> LENGTH: 8
<212> TYPE: PRT
<213> ORGANISM: Unknown Organism
<220> FEATURE:
<223> OTHER INFORMATION: Description of Unknown Organism: Unknown
      transforming protein ras (teratocarcinoma)

<400> SEQUENCE: 69

Lys Lys Lys His Thr Val Lys Lys
 1               5

<210> SEQ ID NO 70
<211> LENGTH: 9
<212> TYPE: PRT
<213> ORGANISM: Unknown Organism
```

```
<220> FEATURE:
<223> OTHER INFORMATION: Description of Unknown Organism: Unknown
      TRAF-associated NFkB activator peptide

<400> SEQUENCE: 70

Lys Ala Gln Lys Asp His Leu Ser Lys
  1               5

<210> SEQ ID NO 71
<211> LENGTH: 10
<212> TYPE: PRT
<213> ORGANISM: Unknown Organism
<220> FEATURE:
<223> OTHER INFORMATION: Description of Unknown Organism: Unknown RFP
      transforming protein

<400> SEQUENCE: 71

His Leu Lys Arg Val Lys Asp Leu Lys Lys
  1               5                  10

<210> SEQ ID NO 72
<211> LENGTH: 11
<212> TYPE: PRT
<213> ORGANISM: Unknown Organism
<220> FEATURE:
<223> OTHER INFORMATION: Description of Unknown Organism: Unknown
      transforming protein

<400> SEQUENCE: 72

Lys Tyr Gly Ser Pro Lys His Arg Leu Ile Lys
  1               5                  10

<210> SEQ ID NO 73
<211> LENGTH: 13
<212> TYPE: PRT
<213> ORGANISM: Papilloma virus type 11

<400> SEQUENCE: 73

Lys Leu Lys His Ile Leu Gly Lys Ala Arg Phe Ile Lys
  1               5                  10

<210> SEQ ID NO 74
<211> LENGTH: 12
<212> TYPE: PRT
<213> ORGANISM: Unknown Organism
<220> FEATURE:
<223> OTHER INFORMATION: Description of Unknown Organism: Unknown
      tyrosine kinasc protein

<400> SEQUENCE: 74

Lys Gly Asp His Val Lys His Tyr Lys Ile Arg Lys
  1               5                  10

<210> SEQ ID NO 75
<211> LENGTH: 13
<212> TYPE: PRT
<213> ORGANISM: Unknown Organism
<220> FEATURE:
<223> OTHER INFORMATION: Description of Unknown Organism: Unknown
      transforming protein

<400> SEQUENCE: 75

Lys Glu Lys Leu Arg Asp Val Met Val Asp Arg His Lys
  1               5                  10
```

```
<210> SEQ ID NO 76
<211> LENGTH: 15
<212> TYPE: PRT
<213> ORGANISM: Unknown Organism
<220> FEATURE:
<223> OTHER INFORMATION: Description of Unknown Organism: Unknown
      transforming protein

<400> SEQUENCE: 76

Lys Leu Gln Ala Arg Gln Gln Gln Leu Leu Lys Lys Ile Glu His
 1               5                  10                  15

<210> SEQ ID NO 77
<211> LENGTH: 14
<212> TYPE: PRT
<213> ORGANISM: Unknown Organism
<220> FEATURE:
<223> OTHER INFORMATION: Description of Unknown Organism: Unknown
      fibroblast growth factor 4 peptide

<400> SEQUENCE: 77

Lys Lys Gly Asn Arg Val Ser Pro Thr Met Lys Val Thr His
 1               5                  10

<210> SEQ ID NO 78
<211> LENGTH: 9
<212> TYPE: PRT
<213> ORGANISM: Unknown Organism
<220> FEATURE:
<223> OTHER INFORMATION: Description of Unknown Organism: Unknown
      Matrix metalloproteinase 7 peptide

<400> SEQUENCE: 78

Lys Glu Ile Pro Leu His Phe Arg Lys
 1               5

<210> SEQ ID NO 79
<211> LENGTH: 8
<212> TYPE: PRT
<213> ORGANISM: Unknown Organism
<220> FEATURE:
<223> OTHER INFORMATION: Description of Unknown Organism: Unknown
      transcription factor 7-like peptide

<400> SEQUENCE: 79

Lys Lys Lys Pro His Ile Lys Lys
 1               5

<210> SEQ ID NO 80
<211> LENGTH: 9
<212> TYPE: PRT
<213> ORGANISM: Unknown Organism
<220> FEATURE:
<223> OTHER INFORMATION: Description of Unknown Organism: Unknown breast
      cancer antigen peptide

<400> SEQUENCE: 80

Lys Thr Arg His Asp Pro Leu Ala Lys
 1               5

<210> SEQ ID NO 81
<211> LENGTH: 10
<212> TYPE: PRT
<213> ORGANISM: Unknown Organism
<220> FEATURE:
<223> OTHER INFORMATION: Description of Unknown Organism: Unknown
      BRCA-1-Associated protein
```

```
<400> SEQUENCE: 81

Lys His His Pro Lys Asp Asn Leu Ile Lys
 1               5                  10

<210> SEQ ID NO 82
<211> LENGTH: 10
<212> TYPE: PRT
<213> ORGANISM: Unknown Organism
<220> FEATURE:
<223> OTHER INFORMATION: Description of Unknown Organism: Unknown
      autoantigen peptide

<400> SEQUENCE: 82

Lys His Lys Arg Lys Lys Phe Arg Gln Lys
 1               5                  10

<210> SEQ ID NO 83
<211> LENGTH: 10
<212> TYPE: PRT
<213> ORGANISM: Unknown Organism
<220> FEATURE:
<223> OTHER INFORMATION: Description of Unknown Organism: Unknown Glioma
      Replikin peptide

<400> SEQUENCE: 83

Lys Ala Gly Val Ala Phe Leu His Lys Lys
 1               5                  10

<210> SEQ ID NO 84
<211> LENGTH: 10
<212> TYPE: PRT
<213> ORGANISM: Unknown Organism
<220> FEATURE:
<223> OTHER INFORMATION: Description of Unknown Organism: Unknown
      ovarian cancer antigen peptide

<400> SEQUENCE: 84

Lys His Lys Arg Lys Lys Phe Arg Gln Lys
 1               5                  10

<210> SEQ ID NO 85
<211> LENGTH: 10
<212> TYPE: PRT
<213> ORGANISM: Unknown Organism
<220> FEATURE:
<223> OTHER INFORMATION: Description of Unknown Organism: Unknown EE L
      leukemia peptide

<400> SEQUENCE: 85

Lys Lys Lys Ser Lys Lys His Lys Asp Lys
 1               5                  10

<210> SEQ ID NO 86
<211> LENGTH: 11
<212> TYPE: PRT
<213> ORGANISM: Unknown Organism
<220> FEATURE:
<223> OTHER INFORMATION: Description of Unknown Organism: Unknown
      Poto-oncogene peptide

<400> SEQUENCE: 86

His Lys Ser Glu Lys Pro Ala Leu Pro Arg Lys
 1               5                  10

<210> SEQ ID NO 87
<211> LENGTH: 14
<212> TYPE: PRT
<213> ORGANISM: Unknown Organism
```

```
<220> FEATURE:
<223> OTHER INFORMATION: Description of Unknown Organism: Unknown
      adenomatosis polyposis coli peptide

<400> SEQUENCE: 87

Lys Lys Lys Lys Pro Ser Arg Leu Lys Gly Asp Asn Glu Lys
1               5                   10

<210> SEQ ID NO 88
<211> LENGTH: 16
<212> TYPE: PRT
<213> ORGANISM: Unknown Organism
<220> FEATURE:
<223> OTHER INFORMATION: Description of Unknown Organism: Unknown
      gastric cancer transforming protein

<400> SEQUENCE: 88

Lys Thr Lys Lys Gly Asn Arg Val Ser Pro Thr Met Lys Val Thr His
1               5                   10                  15

<210> SEQ ID NO 89
<211> LENGTH: 18
<212> TYPE: PRT
<213> ORGANISM: Unknown Organism
<220> FEATURE:
<223> OTHER INFORMATION: Description of Unknown Organism: Unknown K-RAS
      2B transforming protein

<400> SEQUENCE: 89

Lys His Lys Glu Lys Met Ser Lys Asp Gly Lys Lys Lys Lys Lys
1               5                   10                  15

Ser Lys

<210> SEQ ID NO 90
<211> LENGTH: 29
<212> TYPE: PRT
<213> ORGANISM: Influenza virus

<400> SEQUENCE: 90

Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25

<210> SEQ ID NO 91
<211> LENGTH: 29
<212> TYPE: PRT
<213> ORGANISM: Influenza virus

<400> SEQUENCE: 91

Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25

<210> SEQ ID NO 92
<211> LENGTH: 29
<212> TYPE: PRT
<213> ORGANISM: Influenza virus

<400> SEQUENCE: 92

Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25
```

-continued

```
<210> SEQ ID NO 93
<211> LENGTH: 29
<212> TYPE: PRT
<213> ORGANISM: Influenza virus

<400> SEQUENCE:

-continued

```
<400> SEQUENCE: 98

Lys Lys Asn Ser Thr Tyr Pro Thr Ile Lys Arg Ser Tyr Asn Asn Thr
  1               5                  10                  15
Asn Gln Glu Asp Leu Leu Val Leu Trp Gly Ile His His
             20                  25

<210> SEQ ID NO 99
<211> LENGTH: 29
<212> TYPE: PRT
<213> ORGANISM: Influenza virus

<400> SEQUENCE: 99

Lys Lys Asn Ser Thr Tyr Pro Thr Ile Lys Arg Ser Tyr Asn Asn Thr
  1               5                  10                  15
Asn Gln Glu Asp Leu Leu Val Leu Trp Gly Ile His His
             20                  25

<210> SEQ ID NO 100
<211> LENGTH: 29
<212> TYPE: PRT
<213> ORGANISM: Influenza virus

<400> SEQUENCE: 100

Lys Lys Asn Ser Thr Tyr Pro Thr Ile Lys Arg Ser Tyr Asn Asn Thr
  1               5                  10                  15
Asn Gln Glu Asp Leu Leu Val Leu Trp Gly Ile His His
             20                  25

<210> SEQ ID NO 101
<211> LENGTH: 29
<212> TYPE: PRT
<213> ORGANISM: Influenza virus

<400> SEQUENCE: 101

Lys Lys Asn Asn Ala Tyr Pro Thr Ile Lys Arg Ser Tyr Asn Asn Thr
  1               5                  10                  15
Asn Gln Glu Asp Leu Leu Val Leu Trp Gly Ile His His
             20                  25

<210> SEQ ID NO 102
<211> LENGTH: 29
<212> TYPE: PRT
<213> ORGANISM: Influenza virus

<400> SEQUENCE: 102

Lys Lys Asn Ser Thr Tyr Pro Thr Ile Lys Arg Ser Tyr Asn Asn Thr
  1               5                  10                  15
Asn Gln Glu Asp Leu Leu Val Met Trp Gly Ile His His
             20                  25

<210> SEQ ID NO 103
<211> LENGTH: 29
<212> TYPE: PRT
<213> ORGANISM: Influenza virus

<400> SEQUENCE: 103

Lys Lys Asn Ser Ala Tyr Pro Thr Ile Lys Arg Ser Tyr Asn Asn Thr
  1               5                  10                  15
Asn Gln Glu Asp Leu Leu Val Leu Trp Gly Ile His His
             20                  25
```

<210> SEQ ID NO 104
<211> LENGTH: 29
<212> TYPE: PRT
<213> ORGANISM: Influenza virus

<400> SEQUENCE: 104

Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25

<210> SEQ ID NO 105
<211> LENGTH: 29
<212> TYPE: PRT
<213> ORGANISM: Influenza virus

<400> SEQUENCE: 105

Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25

<210> SEQ ID NO 106
<211> LENGTH: 29
<212> TYPE: PRT
<213> ORGANISM: Influenza virus

<400> SEQUENCE: 106

Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile Gln His
            20                  25

<210> SEQ ID NO 107
<211> LENGTH: 29
<212> TYPE: PRT
<213> ORGANISM: Influenza virus

<400> SEQUENCE: 107

Lys Lys Asn Ser Ala Tyr Pro Ile Ile Lys Arg Ser Tyr Asn Asn Thr
1               5                   10                  15

Asn Gln Glu Asp Leu Leu Val Leu Trp Gly Ile His His
            20                  25

<210> SEQ ID NO 108
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Met Asp Glu Leu
1